United States Patent
Yang et al.

(10) Patent No.: US 11,124,760 B2
(45) Date of Patent: Sep. 21, 2021

(54) METHODS FOR OVERCOMING GLUTAMINE DEPRIVATION DURING MAMMALIAN CELL CULTURE

(71) Applicants: Biogen MA Inc., Cambridge, MA (US); Samsung Bioepis, Incheon (KR)

(72) Inventors: William Yang, Cary, NC (US); Yao-Ming Huang, Cary, NC (US); Marty Sinacore, Andover, MA (US); Thomas Ryll, Lexington, MA (US); Jiuyi Lu, Ipswich, MA (US); Jaesun Lee, Incheon (KR); Kyngju Lee, Incheon (KR); Hyoung Taek Lim, Incheon (KR); Eunchong Yang, Seoul (KR)

(73) Assignees: Biogen MA Inc., Cambridge, MA (US); Samsung Bioepis, Yeonsu-gu (KR)

( * ) Notice: Subject to any disclaimer, the term of this patent is extended or adjusted under 35 U.S.C. 154(b) by 156 days.

(21) Appl. No.: 15/128,732

(22) PCT Filed: Mar. 24, 2015

(86) PCT No.: PCT/US2015/022259
§ 371 (c)(1),
(2) Date: Sep. 23, 2016

(87) PCT Pub. No.: WO2015/148515
PCT Pub. Date: Oct. 1, 2015

(65) Prior Publication Data
US 2017/0175075 A1 Jun. 22, 2017

Related U.S. Application Data

(60) Provisional application No. 61/969,800, filed on Mar. 24, 2014.

(51) Int. Cl.
*C12N 5/00* (2006.01)
*C12P 21/00* (2006.01)

(52) U.S. Cl.
CPC ............ *C12N 5/0018* (2013.01); *C12P 21/00* (2013.01); *C12N 2500/40* (2013.01); *C12N 2500/60* (2013.01)

(58) Field of Classification Search
CPC .............. C12N 5/0018; C12N 2500/60; C12N 2500/40; C12P 21/00
See application file for complete search history.

(56) References Cited

U.S. PATENT DOCUMENTS

| | | |
|---|---|---|
| 4,560,655 A | 12/1985 | Baker |
| 4,657,866 A | 4/1987 | Kumar |
| 4,767,704 A | 8/1988 | Cleveland et al. |
| 4,927,762 A | 5/1990 | Darfler |
| 5,122,469 A | 6/1992 | Mather et al. |
| 5,223,409 A | 6/1993 | Ladner et al. |
| 5,225,539 A | 7/1993 | Winter |
| 5,585,089 A | 12/1996 | Queen et al. |
| 5,624,821 A | 4/1997 | Winter et al. |
| 5,648,260 A | 7/1997 | Winter et al. |
| 5,658,727 A | 8/1997 | Barbas et al. |
| 5,667,988 A | 9/1997 | Barbas et al. |
| 5,693,761 A | 12/1997 | Queen et al. |
| 5,693,762 A | 12/1997 | Queen et al. |
| 5,859,205 A | 1/1999 | Adair et al. |
| 5,869,046 A | 2/1999 | Presta et al. |
| 5,885,793 A | 3/1999 | Griffiths et al. |
| 6,407,213 B1 | 6/2002 | Carter et al. |
| 7,785,880 B2 | 8/2010 | Goldenberg et al. |
| 2003/0070185 A1 | 4/2003 | Jakobovits et al. |
| 2005/0037000 A1 | 2/2005 | Stavenhagen et al. |
| 2005/0079574 A1 | 4/2005 | Bond |
| 2008/0254513 A1 | 10/2008 | Cayli |
| 2010/0221781 A1 | 9/2010 | Kopetzki et al. |

FOREIGN PATENT DOCUMENTS

| | | |
|---|---|---|
| CN | 101603026 A | 12/2009 |
| WO | WO-8700195 A1 | 1/1987 |
| WO | WO-8705330 A1 | 9/1987 |
| WO | WO-9002809 A1 | 3/1990 |
| WO | WO-9003430 A1 | 4/1990 |
| WO | WO-9117271 A1 | 11/1991 |
| WO | WO-9201047 A1 | 1/1992 |
| WO | WO-9209690 A2 | 6/1992 |
| WO | WO-9215679 A1 | 9/1992 |
| WO | WO-9218619 A1 | 10/1992 |
| WO | WO-9220791 A1 | 11/1992 |
| WO | WO-9301288 A1 | 1/1993 |

(Continued)

OTHER PUBLICATIONS

SIGMA, 1998, Hypoxanthine-Aminopterin-Thymidine (HAT) media, Product Information Sheet, one page.*
Kim et al., Process Biochemistry, 2012, vol. 47, p. 2557-2561, published online on Aug. 2012, and supplementary Table 1.*
HyClone "Cell Boost 2" Supplement data file No. 29-1368-19 AA, 4 pages of PDF, downloaded on Sep. 25, 2018.*
HyClone "SFM4CHO" Media Description 2 pages of PDF, downloaded on Sep. 25, 2018.*
Engström et al., Journal of Cellular Physiology, 1984, vol. 120, p. 233-241.*
Chen et al., Appl. Microbiol Biotechnol., 2012, vol. 93, p. 169-178.*
SIGMA-ALDRICH online catalogue, D6421, SIGMA-ALDRICH Dulbecco's Modified Eagle's Medium/Nutrient Mixture F-12 Ham, retrieved from sigmaaldrich.com on Jun. 13, 2019, 4 pages of PDF.*
Hernandez et al., Biotechnol., 2010, vol. 5, p. 1090-1097.*
International Preliminary Report on Patentability for Application No. PCT/US2015/022259 dated Oct. 6, 2016.

(Continued)

*Primary Examiner* — Kade Ariani
(74) *Attorney, Agent, or Firm* — Wolf, Greenfield & Sacks, P.C.

(57) ABSTRACT

The present invention pertains to methods of producing polypeptide of interest in cell cultures lacking glutamine. The present invention further pertains to a method of producing a protein of interest in a large scale cell culture, comprising supplementing the cell culture with nucleic acid synthesis precursors and/or corticosteroids.

18 Claims, 7 Drawing Sheets

(56) References Cited

FOREIGN PATENT DOCUMENTS

Figure 1:
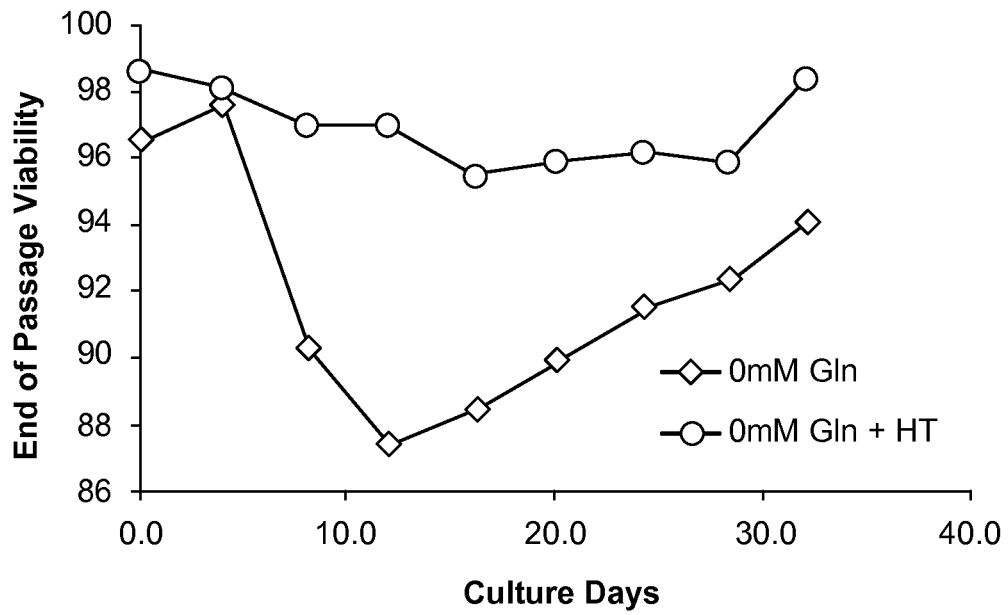

| WO | WO 93/13196 A2 | 7/1993 |
|----|----|----|
| WO | WO-9633735 A1 | 10/1996 |
| WO | WO-9634096 A1 | 10/1996 |
| WO | WO 2009/087087 A1 | 7/2009 |
| WO | WO-2011019619 A1 | 2/2011 |
| WO | WO 2011/044180 * | 4/2011 |
| WO | WO 2015/026846 A1 | 2/2015 |

OTHER PUBLICATIONS

Altamirano, C. et al., "Improvement of CHO Cell Culture Medium Formulation: Simultaneous Substitution of Glucose and Glutamine," *Biotechnol. Prog.* 16(1):69-75, American Chemical Society and American Institute of Chemical Engineers, United States (2000).

Altamirano, C. et al.,"Strategies for fed-batch cultivation of t-PA producing CHO cells: substitution of glucose and glutamine and rational design of culture medium," *J. Biotechnol.* 110(2):171-179, Elsevier B.V., Netherlands (2004).

Angal, S. et al., "A Single Amino Acid Substitution Abolishes the Heterogeneity of Chimeric Mouse/Human (IgG4) Antibody," *Molec. Immunol.* 30(1):105-108, Pergamon Press Ltd., Great Britain (1993).

Aplin, J.D. and Wriston, J.C., "Preparation, Properties, and Applications of Carbohydrate Conjugates of Proteins and Lipids," *Crit. Rev. Biochem. Mol. Biol.* 10(4):259-306, CRC Press, United States (1981).

Barnes, D. and Sato, G., "Methods for Growth of Cultured Cells in Serum-Free Medium," *Anal. Biochem.* 102(2):255-270, Academic Press, Inc., United States (1980).

Berge, S.M. et al., "Pharmaceutical Salts," *J. Pharm. Sci.* 66(1):1-19, John Wiley & Sons, United States (1977).

Chen, F., et al., "Insight into the roles of hypoxanthine and thymidine on cultivating antibody-producing CHO cells: cell growth, antibody production and long-term stability," *Appl. Microbiol. Biotechnol.* 93(1):169-178, Springer International, Germany (2012).

Chiang, G.G. and Sisk, W.P., "Bcl-x $_L$ Mediates Increased Production of Humanized Monoclonal Antibodies in Chinese Hamster Ovary Cells," *Biotechnol. Bioeng.* 91(7):779-792, Wiley Periodicals, Inc., United States (2005).

Davies, J. and Riechmann, L., "Single antibody domains as small recognition units: design and in vitro antigen selection of camelized, human VH domains with improved protein stability," *Protein Engin.* 9(6):531-537, Oxford University Press, Great Britain (1996).

De Vries, C. et al., "The fms-Like Tyrosine Kinase, a Receptor for Vascular Endothelial Growth Factor," *Science* 255(5047):989-991, American Association for the Advancement of Science, United States (1992).

Edge, A.S.B. et al., "Deglycosylation of Glycoproteins by Trifluoromethanesulfonic Acid," *Anal. Biochem.* 118(I):131-137, Academic Press, Inc., United States (1981).

Graham F.L. et al., "Characteristics of a Human Cell Line Transformed by DNA from Human Adenovirus Type 5," *J. Gen. Virol.* 36(1):59-74, Society for General Microbiology, Great Britain (1977).

Green, L.L. et al., "Antigen-specific human monoclonal antibodies from mice engineered with human Ig heavy and light chain YACs," *Nat. Genet.* 7(1):13-21, Nature Publishing Company, United States (1994).

Hakimuddin, T. and Bahl, O.P. "A Chemical Method for the Deglycosylation of Proteins," *Arch. Biochem. Biophys.* 259(1):52-57, Academic Press, Inc., United States (1987).

Ham, R.G. and Mckeehan, W.L., "Media and Growth Requirements," in *Meth. Enzymol.*, vol. 58, Jakoby, W.B. and Pastan, I.H., eds., pp. 44-93, Academic Press, Inc., United States (1979).

Huang, Y.-M. et al., "Maximizing Productivity of CHO Cell-Based Fed-Batch Culture Using Chemically Defined Media Conditions and Typical Manufacturing Equipment," *Biotechnol. Prog.* 26(5):1400-1410, American Institute of Chemical Engineers, United States (2010).

International Search Report and Written Opinion for International Application No. PCT/US2015/022259, 15 pages, European Patent Office, Rijswijk, Netherlands, dated Aug. 13, 2015.

Johnson, L.V. et al., "Localization of mitochondria in living cells with rhodamine 123," *Proc. Natl. Acad. Sci. U.S.A.* 77(2):990-994, National Academy of Sciences, United States (1980).

Kshirsagar, R. et al., "Controlling Trisulfide Modification in Recombinant Monoclonal Antibody Produced in Fed-Batch Cell Culture," *Biotechnol. Bioeng.* 109(10):2523-2532, Wiley Periodicals, Inc., United States (2012).

Luo, Y. and Chen, G., "Combined Approach of NMR and Chemometrics for Screening Peptones Used in the Cell Culture Medium for the Production of a Recombinant Therapeutic Protein," *Biotechnol. Bioeng.* 97(6):1654-1659, Wiley Periodicals, Inc., United States (2007).

Ma, N. et al., "A Single Nutrient Feed Supports Both Chemically Defined NS0 and CHO Fed-Batch Processes: Improved Productivity and Lactate Metabolism," *Biotechnol. Prog.* 25(5):1353-1363, American Institute of Chemical Engineers, United States (2009).

Mather, J.P., "Establishment and Characterization of Two Distinct Mouse Testicular Epithelial Cell Lines," *Biol. Reprod.* 23(1):243-252, Society for the Study of Reproduction, United States (1980).

Mather, J.P. et al., "Culture of Testicular Cells in Hormone-Supplemented Serum-Free Medium," *Ann. N. Y. Acad. Sci.* 383:44-68, Blackwell, United States (1982).

Miller, W.M. et al., "A Kinetic Analysis of Hybridoma Growth and Metabolism in Batch and Continuous Suspension Culture: Effect of Nutrient Concentration, Dilution Rate, and pH," *Biotechnol. Bioeng.* 32(8):947-965, John Wiley & Sons, Inc., United States (1988).

Milstein, C. and Cuello, A.C., "Hybrid hybridomas and their use in immunohistochemistry," *Nature* 305 (5934):537-540, Macmillan Journals, Ltd., Great Britain (1983).

Morrison, S.L., "Transfectomas Provide Novel Chimeric Antibodies," *Science* 229(4719):1202-1207, Association for the Advancement of Science, United States (1985).

Mustonen, T. and Alitalo, K., "Endothelial Receptor Tyrosine Kinases Involved in Angiogenesis," *J. Cell Biol.* 129(4):895-898, The Rockefeller University Press, United States (1995).

Oi, V.T. and Morrison, S.L., "Chimeric Antibodies," *BioTechniques* 4(3):214-221, Informa BioSciences, United States (1986).

Porter, A.J. et al., "Strategies for Selecting Recombinant CHO Cell Lines for cGMP Manufacturing: Realizing the Potential in Bioreactors," *Biotechnol. Prog.* 26(5):1446-1454, American Institute of Chemical Engineers, United States (2010).

Sanfeliu, A. and Stephanopoulos, G., "Effect of Glutamine Limitation on the Death of Attached Chinese Hamster Ovary Cells," *Biotechnol. Bioeng.* 64(1):46-53, John Wiley & Sons, Inc., United States (1999).

Sato, T.N. et al., "Distinct roles of the receptor tyrosine kinases Tie-1 and Tie-2 in blood vessel formation," *Nature* 376(6535):70-74, Nature Publishing Group, Great Britain (1995).

Schneider, M. et al., "The importance of ammonia in mammalian cell culture," *J. Biotechnol.* 46(3):161-185, Elsevier Science B.V., Netherlands (1996).

Shibuya, M. et al., "Nucleotide sequence and expression of a novel human receptor-type tyrosine kinase gene (flt) closely related to the fms Family," *Oncogene* 5(4):519-524, Macmillan Press Ltd., Great Britain (1990).

Smith, G.P., "Filamentous Fusion Phage: Novel Expression Vectors That Display Cloned Antigens on the Virion Surface," *Science* 228(4705):1315-1317, American Association for the Advancement of Science, United States (1985).

Terman, B.I. et al., "Identification of a new endothelial cell growth factor receptor tyrosine kinase," *Oncogene* 6(9):1677-1683, Macmillan Press Ltd, Great Britain (1991).

Thotakura, N.R. and Bahl, O.P., "Enzymatic Deglycosylation of Glycoproteins," *Meth. Enzymol.* 138:350-359, Academic Press, Inc. United States (1987).

Ullrich, A. and Schlessinger, J., "Signal Transduction by Receptors with Tyrosine Kinase Activity," *Cell* 61(2):203-212, Cell Press, United States (1990).

(56) References Cited

OTHER PUBLICATIONS

Urlaub, G. and Chasin, L.A., "Isolation of Chinese hamster cell mutants deficient in dihydrofolate reductase activity," *Proc. Natl. Acad. Sci. U.S.A.* 77(7):4216-4220, National Academy of Sciences, United States (1980).

Yarden, Y. and Ullrich, A., "Growth Factor Receptor Tyrosine Kinases," *Ann. Rev. Biochem.* 57:443-478, Annual Reviews Inc., United States (1988).

Yu, M. et al., "Understanding the Intracellular Effect of Enhanced Nutrient Feeding Toward High Titer Antibody Production Process," *Biotechnol. Bioeng.* 108(5):1078-1088, Wiley Periodicals, Inc., United States (2010).

Thotakura et al., Enzymatic Deglycosylation of Glycoproteins. Methods Enzymol. 1987;138:350-9.

Ullrich et al., Signal transduction by receptors with tyrosine kinase activity. Cell. Apr. 20, 1990;61(2):203-12.

[No Author Listed] Certificate for Analysis for HT Supplement (100X), Catalogue No. 11067. Life Technologies. Aug. 31, 2012. 1 page.

[No Author Listed] Certificate for Analysis for HT Supplement (100X), Catalogue No. 11067. Life Technologies. Jan. 29, 2014. 1 page.

[No Author Listed] SAFC BioSciences Product Information for EX-CELL™ CD CHO Serum-Free Medium, with hypoxanthine, with thymidine, without L-glutamine, Catalog No. 14361C. Sep. 2006. 4 pages.

Bort et al., CHO-K1 host cells adapted to growth in glutamine-free medium by FACS-assisted evolution. Biotechnol J. Oct. 2010;5(10):1090-7.

Bradley et al., Mutagenicity of thymidine to cultured Chinese hamster cells. Nature. Aug. 10, 1978;274(5671):607-8.

Burleigh et al., Synergizing metabolic flux analysis and nucleotide sugar metabolism to understand the control of glycosylation of recombinant protein in CHO cells. BMC Biotechnol. Oct. 18, 2011;11:95. doi: 10.1186/1472-6750-11-95.

Chen et al., Correlation of antibody production rate with glucose and lactate metabolism in Chinese hamster ovary cells. Biotechnol Lett. Mar. 2012;34(3):425-32. doi: 10.1007/s10529-011-0798-y. Epub Nov. 22, 2011.

Kurano et al., Growth behavior of Chinese hamster ovary cells in a compact loop bioreactor. 2. Effects of medium components and waste products. J Biotechnol. Jul. 1990;15(1-2):113-28.

Prentice et al., Improving performance of mammalian cells in fed-batch processes through "bioreactor evolution". Biotechnol Prog. Mar.-Apr. 2007;23(2):458-64. Epub Feb. 21, 2007.

Santiago et al., Targeted gene knockout in mammalian cells by using engineered zinc-finger nucleases. Proc Natl Acad Sci U S A. Apr. 15, 2008;105(15):5809-14.

Taschwer et al., Growth, productivity and protein glycosylation in a CHO EpoFc producer cell line adapted to glutamine-free growth. J Biotechnol. Jan. 20, 2012;157(2):295-303. doi: 10.1016/j.jbiotec.2011.11.014. Epub Dec. 9, 2011.

\* cited by examiner

A.

B.

A.

B.

METHODS FOR OVERCOMING GLUTAMINE DEPRIVATION DURING MAMMALIAN CELL CULTURE

RELATED APPLICATIONS

This application is a national stage filing under 35 U.S.C. § 371 of International Application No. PCT/US2015/022259, filed Mar. 24, 2015, which claims the benefit under 35 U.S.C. § 119(e) of U.S. Provisional Application No. 61/969,800, filed Mar. 24, 2014, the contents of each of which are incorporated herein by reference in their entirety.

BACKGROUND OF THE INVENTION

Field of the Invention

The present invention pertains to a cell culture medium comprising downstream products of glutamine metabolism, such as hypoxanthine and thymidine, adenosine, or corticosteroids, such as dexamethasone, hydrocortisone, or prednisolone, and methods of using thereof. The present invention further pertains to a method of producing a protein of interest in a large scale cell culture containing glutamine-free culture media, comprising supplementing the cell culture with hypoxanthine, thymidine, adenosine, dexamethasone, hydrocortisone, or prednisolone, or mixtures thereof.

Background Art

Over the last few decades, much research has focused on the production of recombinant proteins, e.g., monoclonal antibodies, and the work has taken a variety of angles. While much work in the literature has utilized media containing sera or hydrolysates, chemically defined media were also developed in order to eliminate the problematic lot-to-lot variation of complex components (Luo and Chen, *Biotechnology and Bioengineering* 97(6):1654-1659 (2007)). An improved understanding of the cell culture has permitted a shift to chemically defined medium without compromising on growth, viability, titer, etc. To date optimized chemically defined processes have been reported with titers as high as 7.5-10 g/L (Huang et al., *Biotechnology Progress* 26(5): 1400-1410 (2010); Ma et al., *Biotechnology Progress* 25(5): 1353-1363 (2009); Yu et al., *Biotechnology and Bioengineering* 108(5):1078-1088 (2011)). In general, the high titer chemically defined processes are fed batch processes with cultivation times of 11-18 days. The process intensification has been achieved without compromising product quality while maintaining relatively high viabilities.

Achievement of a robust, scalable production process includes more than increasing the product titer while maintaining high product quality. The process must also predictably require the main carbohydrate source such that the feeding strategy does not need to change across scales. As many processes use glucose as the main carbohydrate, and have lactate and ammonium as the main byproducts, the time course of these three critical chemicals should also scale.

Mammalian cells have become the dominant system for the production of mammalian proteins for clinical applications, primarily due to their ability to produce properly folded and assembled heterologous proteins, and their capacity for posttranslational modifications. It is conventional to have glutamine in cell culture media during recombinant production of heterologous proteins, including antibodies. L-glutamine is an essential amino acid, which is considered the primary energy and nitrogen sources for cells in culture. Most commercially available media are formulated with free L-glutamine which is either included in the basal formula or added to liquid media formulations at the time of use. Thus, all mammalian cell culture media contain glutamine except those for glutamine synthetase transfected cell lines, such as GS NS0 and GS CHO cell lines, where the cells themselves produce the glutamine needed for growth. Glutamine is widely used at various concentrations typically from 1 to 20 mM in base media and much higher concentration in feeds for fed-batch process. For example, the concentration of L-glutamine is 0.5 mM in Ames' Medium and 10 mM in MCDP Media 131. DMEM/Ham's Nutrient Mixture F-12 (50:50) is often used as a starting formulation for proprietary media used with Chinese Hamster Ovary (CHO) cells. L-glutamine in DMEM/Ham's Nutrient Mixture F-12 is 2.5 mM. L-glutamine concentration in Serum-Free/Protein Free Hybridoma Medium is 2.7 mM. L-glutamine in DMEM, GMEM, IMDM and H-Y medium is 4 mM, of which IMDM is often used as a starting formulation for proprietary hybridoma cell culture media. It is generally held that hybridoma cells grow better in concentrations of L-glutamine that are above the average levels found in media. (Dennis R. Conrad, Glutamine in Cell Culture, Sigma-Aldrich Media Expert).

It was shown that glutamine is the main source of ammonia accumulated in cell culture (see review by Markus Schneider, et. al. 1996, Journal of Biotechnology 46:161-185). Thus, lowering glutamine in cell culture media significantly reduced the accumulation of $NH_4^+$ level, resulting in lower cytotoxicity (see Markus Schneider, et. al. 1996, supra). Reduced $NH_4^+$ cytotoxicity resulted in higher cell viability, thus extended culture longevity. Based on an estimated glutamine consumption study using CHO cells, it was suggested that cells may consume glutamine at a rate of 0.3-0.4 mM per day (Miller, et. al. 1988, Biotechnol. Bioeng. 32: 947-965). Altamirano et al. (2001, J. Biotechnol. 110:171-9) studied the effect of glutamine replacement by glutamate and the balance between glutamate and glucose metabolism on the redistribution of CHO cells producing recombinant human tissue plasminogen activator (rhut-PA). When glutamine was replaced with glutamate and balanced with glucose catabolism (carbon and nitrogen ratio, C/N ratio), cell metabolism was found redistributed and forced to utilize carbon and energy source more favorably to production of rhut-PA. It was also reported that CHO cells in adherent cultures can grow in the absence of added glutamine due to endogenous glutamine synthetase activity that allowed cells to synthesize glutamine from glutamic acid in the medium (Sanfeliu and Stephanopoulos, 1999, Biotechnol. Bioeng. 64:46-53). However, compared to control cultures in glutamine-containing media, the cell growth rate in glutamine-free media was slower with an increased fraction of cells distributed in the G0/G1 phase. The depletion of both glutamine and glutamic acid did cause cell death. Thus, there is a need in the art to further improve recombinant protein production processes in glutamine-free culture processes.

BRIEF SUMMARY OF THE INVENTION

The present invention pertains to a method of producing a polypeptide of interest in a glutamine-free cell culture media, comprising culturing mammalian cells expressing the polypeptide of interest in a cell culture medium under conditions that support expression of the polypeptide of interest, wherein said cell culture medium comprises between about 20 μM and about 1000 μM hypoxanthine and between about 2 μM and about 1000 μM thymidine.

In another embodiment, the present invention also pertains to a method of producing a polypeptide of interest in a glutamine-free cell culture media, comprising supplementing the culture with a feed medium comprising a sufficient amount of hypoxanthine and thymidine to increase the hypoxanthine and thymidine concentration in the culture to between about 20 µM and about 1000 µM hypoxanthine and between about 2 µM and about 1000 µM thymidine, wherein the culture comprises cells expressing the polypeptide and a medium, and the cells are maintained under conditions that allow for expression and accumulation of the polypeptide.

In a further embodiment, the present invention pertains to method of producing a polypeptide of interest in a glutamine-free cell culture media, comprising: a) providing a cell culture comprising cells capable of expressing the polypeptide and a medium, b) supplementing the culture with a feed medium comprising a sufficient amount of hypoxanthine and thymidine to increase the hypoxanthine and thymidine concentration in the culture to between about 20 µM and about 1000 µM hypoxanthine and between about 2 µM and about 1000 µM thymidine, and c) maintaining the cells in the hypoxanthine and thymidine supplemented culture of b) under conditions that allow for expression and accumulation of the polypeptide.

In one embodiment, the method further comprises supplementing the culture with adenosine. In certain embodiments, the concentration of adenosine in the medium is between about 10 µM and about 1000 µM.

In another embodiment, the medium in the method further comprises at least one corticosteroid. In certain embodiments, the concentration of corticosteroid is between about 0.5 µM and about 500 µM. In one embodiment, the corticosteroid is dexamethasone, hydrocortisone, or prednisolone.

In one embodiment, the cells in the culture media are maintained for between about 1 day and about 120 days.

In one embodiment, the culture is supplemented with the feed medium between about 1 and about 25 times.

In one embodiment, the cellular viability of cells in the culture media is increased by about 2%, about 3%, about 4%, about 5%, about 6%, about 7%, about 8%, about 9%, about 10%, about 15%, about 20%, about 25%, about 30%, about 35%, or about 40% compared to cell viability of cells in unsupplemented glutamine-free media.

In some embodiments, the cells are selected from the group consisting of CHO cells, HEK cells, NSO cells, PER.C6 cells, 293 cells, Hela cells, and MDCK cells.

In one embodiment, the polypeptide of interest is the polypeptide of interest is selected from the group consisting of: an antibody, an immunoadhesin, a Transforming Growth Factor (TGF) beta superfamily signaling molecule, and a blood clotting factor.

In one embodiment, the total amount of polypeptide produced by the cells is higher than the total amount of polypeptide produced by the cells maintained in a glutamine-free culture medium that is substantially free from hypoxanthine, thymidine, adenosine, or corticosteroids.

BRIEF DESCRIPTION OF THE DRAWINGS/FIGURES

FIG. 1. Addition of hypoxanthine and thymidine to glutamine-free media maintains cell viability. Mammalian cells expressing an immunoadhesin were transferred from glutamine-containing media to glutamine-free media using a 1:5 split ratio on Day 0. Cells were cultured at 36° C., 5% $CO_2$ in 1 L shake flasks and passaged every 4 days using media with or without 100 µM hypoxanthine and 16 µM thymidine (HT).

Figure 2:
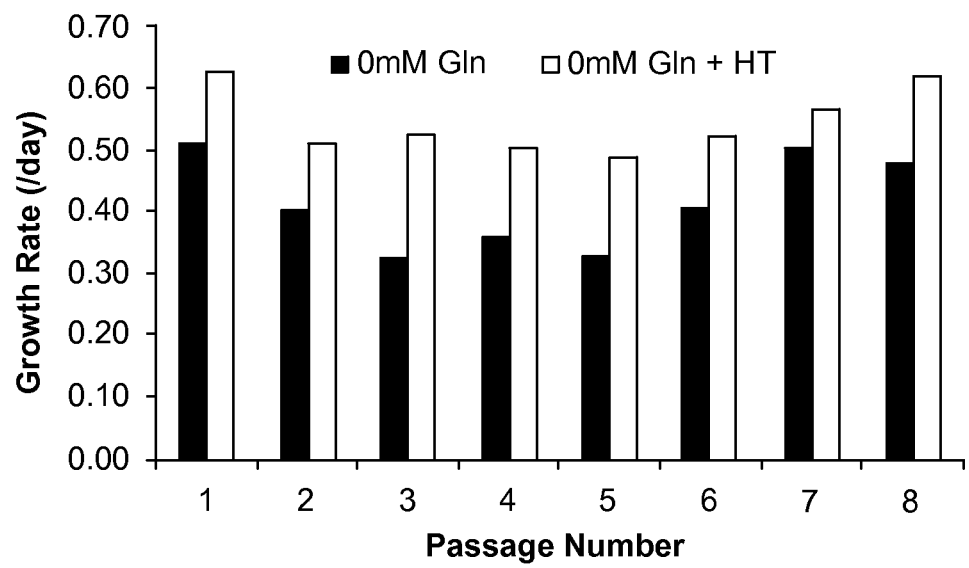

FIG. 2. Addition of hypoxanthine and thymidine (HT) improves growth rate of immunoadhesin-expressing cells in glutamine-free media. Mammalian cells expressing an immunoadhesin were cultured at 36° C., 5% $CO_2$ in 1 L shake flasks and passaged every 4 days using media with or without HT.

Figure 3:
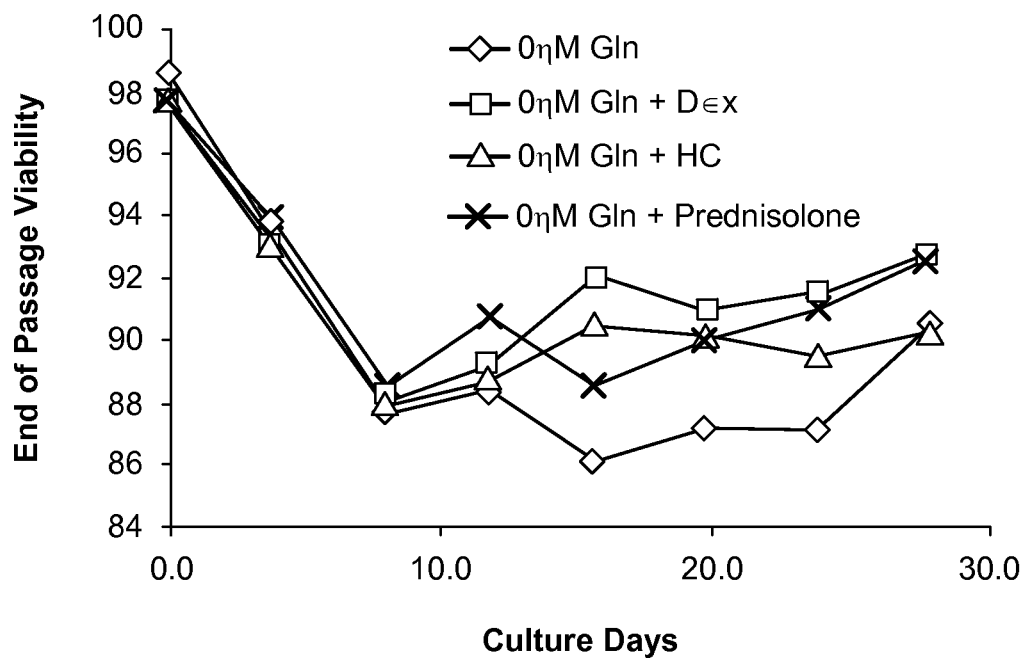

FIG. 3. Corticosteroid addition to glutamine-deprived culture of immunoadhesin-expressing cells hastens viability recovery. Mammalian cells expressing an immunoadhesin were transferred from glutamine-containing media to glutamine-free media using a 1:5 split ratio on Day 0. Cells were cultured at 36° C., 5% $CO_2$ in 1 L shake flasks and passaged every 4 days using media with our without 2.5 µM dexamethasone, hydrocortisone, or prednisolone.

Figure 4:
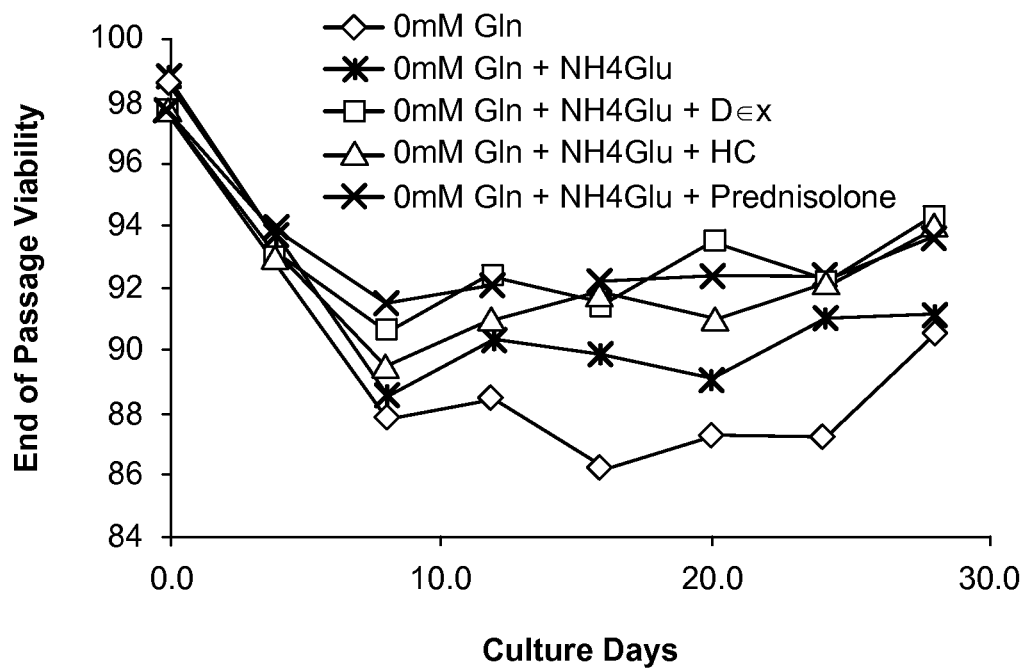

FIG. 4. Addition of corticosteroids, glutamate, and ammonia to glutamine-free cultures of immunoadhesin-expressing cells hastens cell viability recovery. Mammalian cells expressing an immunoadhesin were transferred from glutamine-containing media to glutamine-free media using a 1:5 split ratio on Day 0. Cells were cultured at 36° C., 5% $CO_2$ in 1 L shake flasks and passaged every 4 days using media with or without 2.5 µM dexamethasone, hydrocortisone, or prednisolone in the presence of 2 mM sodium glutamate and 2 mM ammonium chloride.

Figure 5:
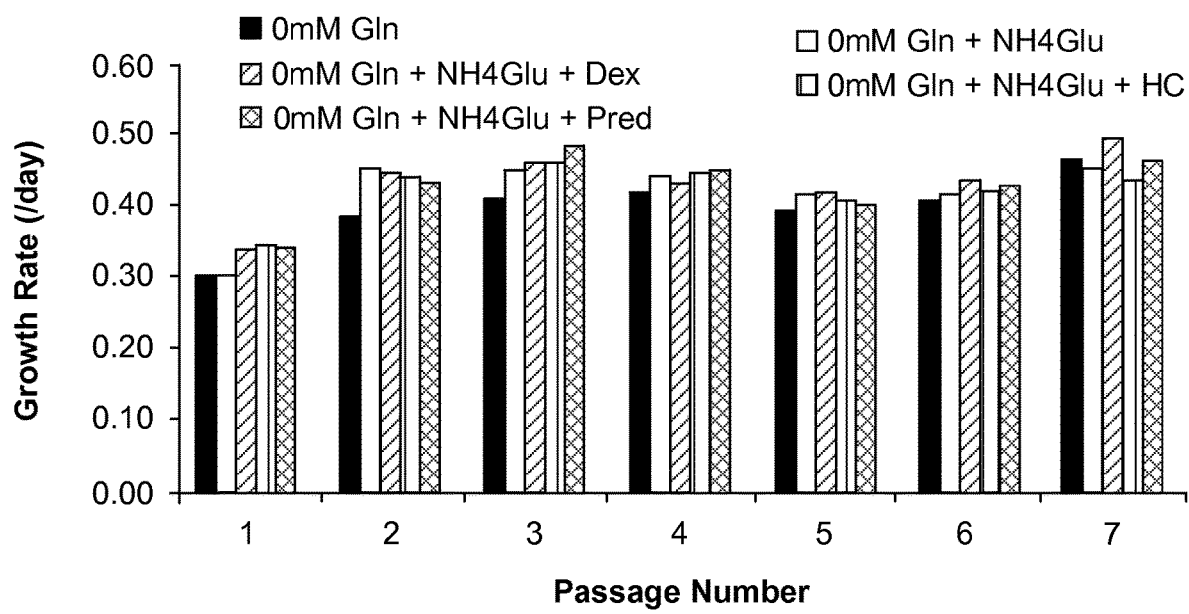

FIG. 5. Addition of corticosteroids, glutamate, and ammonia to glutamine-free cultures of immunoadhesin-expressing cells improves growth rates. Mammalian cells expressing an immunoadhesin were transferred from glutamine-containing media to glutamine-free media using a 1:5 split ratio on Day 0. Cells were cultured at 36° C., 5% $CO_2$ in 1 L shake flasks and passaged every 4 days using media with our without 2.5 µM dexamethasone, hydrocortisone, or prednisolone in the presence of 2 mM sodium glutamate and 2 mM ammonium chloride.

Figure 6:
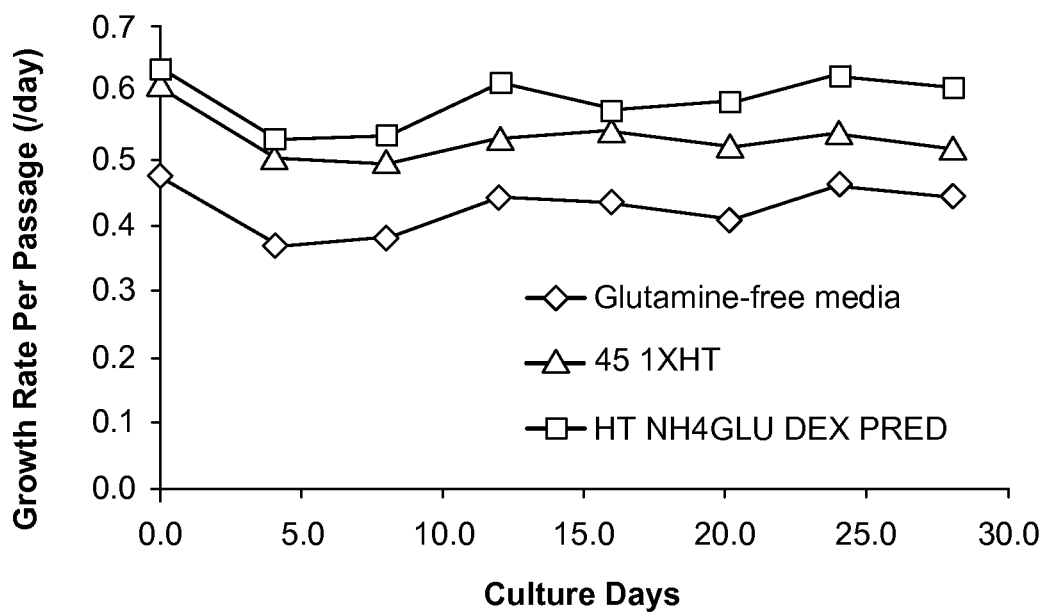
Figure 6:
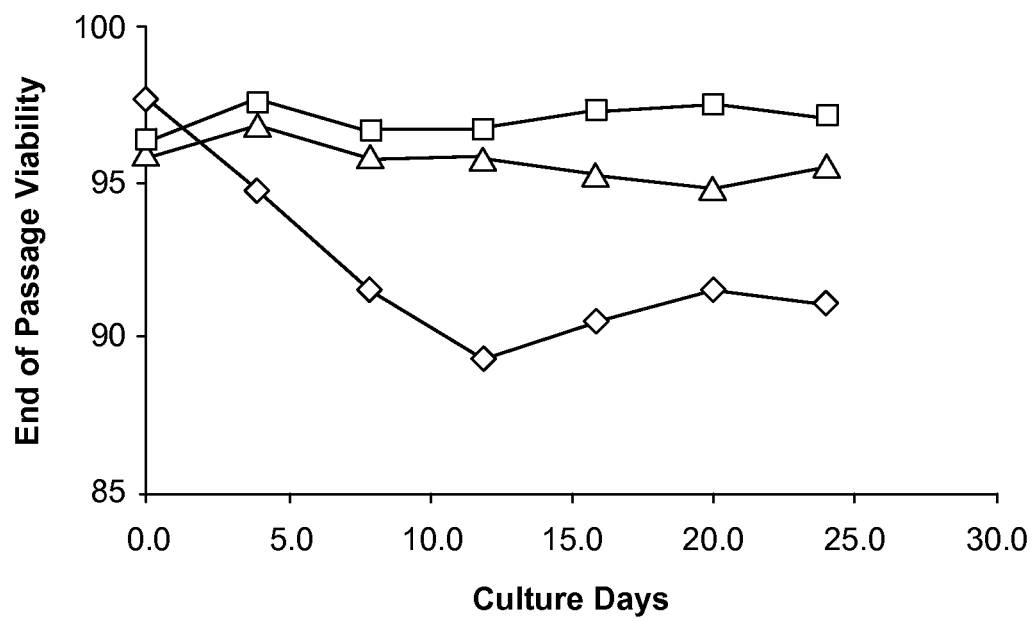

FIG. 6. Addition of hypoxanthine, thymidine, and corticosteroids maintains cell (A) growth and (B) viability during transition to glutamine-free media. Mammalian cells expressing an immunoadhesin were transferred from glutamine-containing media to glutamine-free media using a 1:5 split ratio on Day 0. Cells were cultured at 36° C., 5% $CO_2$ in 1 L shake flasks and passaged every 4 days using glutamine-free media+10 mg/L insulin (circle), glutamine-free media+10 mg/L insulin, 100 µM hypoxanthine, 16 µM thymidine (1×HT, triangle), or glutamine-free media+10 mg/L insulin, 100 µM hypoxanthine, 16 µM thymidine, 2 mM ammonium chloride, 2 mM sodium glutamate, 25 µM dexamethasone, 25 µM prednisolone (HT $NH_4$GLU DEX PRED, square) using a 1:5 split ratio.

Figure 7:
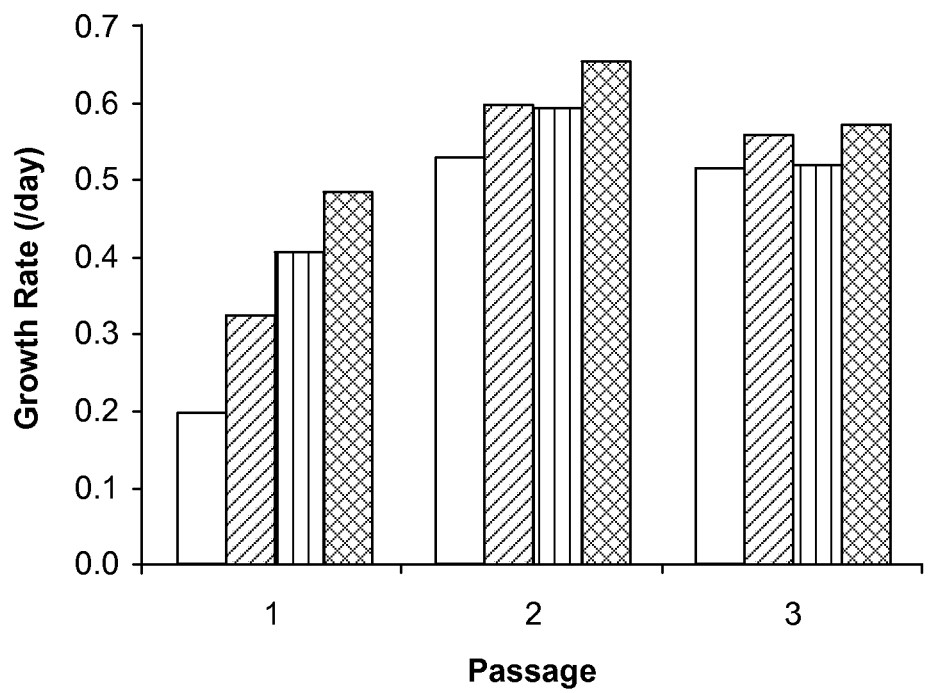
Figure 7:
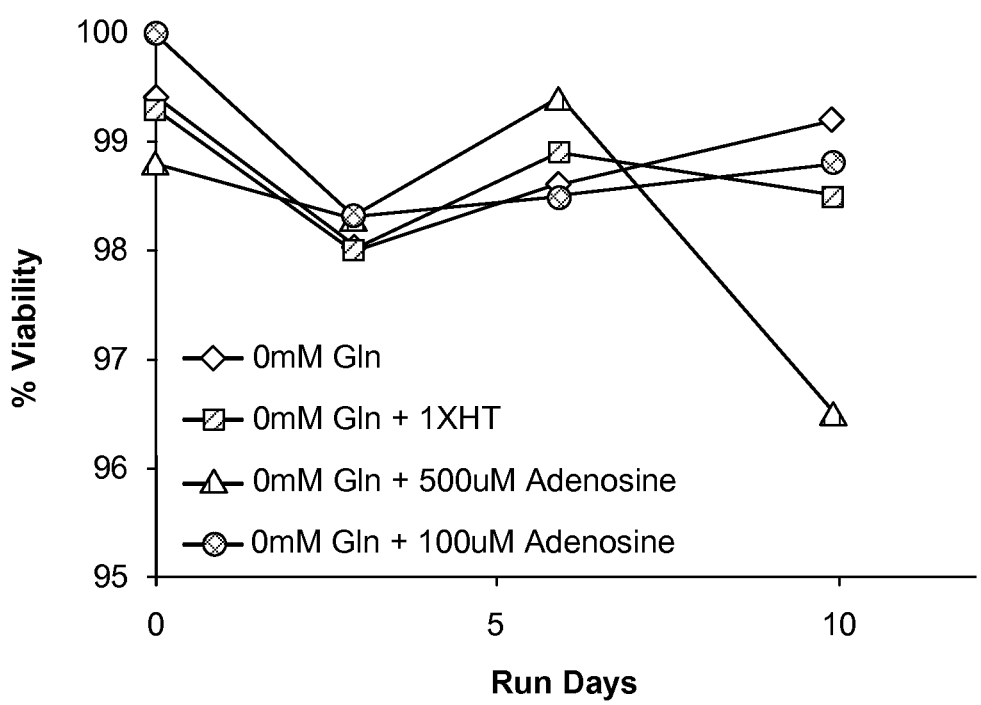

FIG. 7. Addition of hypoxanthine and thymidine (HT), or adenosine, maintains anti alpha-synuclein (A) growth and (B) viability during transition to glutamine-free media. Anti alpha-synuclein cells were transferred from glutamine-containing media to glutamine-free media using a 1:5 split ratio on Day 0. Cells were cultured at 36° C., 5% $CO_2$ in 500 mL shake flasks and passaged every 4 days using glutamine-free media+10 mg/L insulin (first bar in A, diamond in B), glutamine-free media+10 mg/L insulin, 100 µM hypoxanthine, 16 µM thymidine (second bar in A, square in B), glutamine-free media+10 mg/L insulin, 500 µM adenosine (third bar in A, triangle in B), or glutamine-free media+10 mg/L insulin, 100 µM adenosine (fourth bar in A, circle in B), using a 1:5 split ratio.

DETAILED DESCRIPTION OF THE INVENTION

The present invention is based on the recognition that nucleic acid synthesis precursors and/or corticosteroids can maintain cell viability and hasten viability recovery in cell cultures that do not contain glutamine in the growth medium. Glutamine is an alternative energy source for rapidly dividing cells and a precursor for cellular pathways of de novo nucleic acid synthesis. However, other pathways of glutamine metabolism and deamination can lead to undesirable ammonia accumulation which can limit growth, product formation, and product quality. Yet, when deprived of glutamine, mammalian cells experience reduced rates of proliferation and reduced viability, leading to similarly unproductive cultures.

Thus, in one embodiment, nucleic acid synthesis precursors are used to supplement the cell culture to overcome glutamine deprivation. Supplementing the glutamine-deprived cultures with nucleic acid synthesis precursors bypasses the de novo synthesis pathway, enabling cells to maintain high cell viability and the ability to grow quickly in glutamine-free media. In one embodiment, hypoxanthine and thymidine, downstream products of glutamine metabolism, are used to supplement the cultures. In another embodiment, adenosine is used to supplement the cultures.

Corticosteroids increase the expression of endogenous glutamine synthetase, an enzyme that catalyzes the condensation of glutamate with ammonia to form glutamine. Thus, supplementing glutamine-deprived cultures with corticosteroids maintains cellular viability. In one embodiment, the corticosteroids are dexamethasone, hydrocortisone, or prednisolone. Corticosteroids can be used in addition to nucleic acid synthesis precursors to overcome glutamine deprivation.

I. Definitions

The term "antibody" is used to mean an immunoglobulin molecule that recognizes and specifically binds to a target, such as a protein, polypeptide, peptide, carbohydrate, polynucleotide, lipid, or combinations of the foregoing etc., through at least one antigen recognition site within the variable region of the immunoglobulin molecule. As used herein, the term encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, monovalent or monospecific antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively.

As used herein, the term "antibody fragment" refers to a portion of an intact antibody and refers to the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

The term "basal media formulation" or "basal media" as used herein refers to any cell culture media used to culture cells that has not been modified either by supplementation, or by selective removal of a certain component.

The term "batch culture" as used herein refers to a method of culturing cells in which all the components that will ultimately be used in culturing the cells, including the medium (see definition of "medium" below) as well as the cells themselves, are provided at the beginning of the culturing process. A batch culture is typically stopped at some point and the cells and/or components in the medium are harvested and optionally purified.

The term "bioreactor" as used herein refers to any vessel used for the growth of a mammalian cell culture. The bioreactor can be of any size so long as it is useful for the culturing of mammalian cells. Typically, the bioreactor will be at least 1 liter and can be 10, 50, 100, 250, 500, 1000, 2000, 2500, 3000, 5000, 8000, 10,000, 12,0000, 15,000, 20,000, 30,000 liters or more, or any volume in between. For example, a bioreactor will be 10 to 5,000 liters, 10 to 10,000 liters, 10 to 15,000 liters, 10 to 20,000 liters, 10 to 30,000 liters, 50 to 5,000 liters, 50 to 10,000 liters, 50 to 15,000 liters, 50 to 20,000 liters, 50 to 30,000 liters, 1,000 to 5,000 liters, or 1,000 to 3,000 liters. The internal conditions of the bioreactor, including, but not limited to pH and temperature, are typically controlled during the culturing period. The bioreactor can be composed of any material that is suitable for holding mammalian cell cultures suspended in media under the culture conditions of the present invention, including glass, plastic or metal. The term "production bioreactor" as used herein refers to the final bioreactor used in the production of the polypeptide or protein of interest. The volume of the large-scale cell culture production bioreactor is typically at least 500 liters and can be 1000, 2000, 2500, 5000, 8000, 10,000, 12,0000, 15,000 liters or more, or any volume in between. For example, the large scale cell culture reactor will be between about 500 liters and about 20,000 liters, about 500 liters and about 10,000 liters, about 500 liters and about 5,000 liters, about 1,000 liters and about 30,000 liters, about 2,000 liters and about 30,000 liters, about 3,000 liters and about 30,000 liters, about 5,000 liters and about 30,000 liters, or about 10,000 liters and about 30,000 liters, or a large scale cell culture reactor will be at least about 500 liters, at least about 1,000 liters, at least about 2,000 liters, at least about 3,000 liters, at least about 5,000 liters, at least about 10,000 liters, at least about 15,000 liters, or at least about 20,000 liters. One of ordinary skill in the art will be aware of and will be able to choose suitable bioreactors for use in practicing the present invention.

The term "cell density" as used herein refers to that number of cells present in a given volume of medium.

The terms "culture", "cell culture" and "eukaryotic cell culture" as used herein refer to a eukaryotic cell population that is suspended in a medium (see definition of "medium" below) under conditions suitable to survival and/or growth of the cell population. As will be clear to those of ordinary skill in the art, these terms as used herein can refer to the combination comprising the mammalian cell population and the medium in which the population is suspended.

The term "fed-batch culture" as used herein refers to a method of culturing cells in which additional components are provided to the culture at some time subsequent to the beginning of the culture process. A fed-batch culture can be started using a basal medium. The culture medium with which additional components are provided to the culture at some time subsequent to the beginning of the culture process is a feed medium. A fed-batch culture is typically stopped at some point and the cells and/or components in the medium are harvested and optionally purified.

"Growth phase" of the cell culture refers to the period of exponential cell growth (the log phase) where cells are generally rapidly dividing. During this phase, cells are cultured for a period of time, usually between 1-4 days, and under such conditions that cell growth is maximized. The determination of the growth cycle for the host cell can be determined for the particular host cell envisioned without undue experimentation. "Period of time and under such conditions that cell growth is maximized" and the like, refer to those culture conditions that, for a particular cell line, are determined to be optimal for cell growth and division. During the growth phase, cells are cultured in nutrient medium containing the necessary additives generally at about 25°-40° C., in a humidified, controlled atmosphere, such that optimal growth is achieved for the particular cell line. Cells are maintained in the growth phase for a period of about between one and four days, usually between two to three days. The length of the growth phase for the particular cells can be determined without undue experimentation. For example, the length of the growth phase will be the period of time sufficient to allow the particular cells to reproduce to a viable cell density within a range of about 20%-80% of the maximal possible viable cell density if the culture was maintained under the growth conditions.

"Production phase" of the cell culture refers to the period of time during which cell growth has plateaued. During the production phase, logarithmic cell growth has ended and protein production is primary. During this period of time the medium is generally supplemented to support continued protein production and to achieve the desired glycoprotein product.

The term "expression" or "expresses" are used herein to refer to transcription and translation occurring within a host cell. The level of expression of a product gene in a host cell can be determined on the basis of either the amount of corresponding mRNA that is present in the cell or the amount of the protein encoded by the product gene that is produced by the cell. For example, mRNA transcribed from a product gene is desirably quantitated by northern hybridization. Sambrook et al., Molecular Cloning: A Laboratory Manual, pp. 7.3-7.57 (Cold Spring Harbor Laboratory Press, 1989). Protein encoded by a product gene can be quantitated either by assaying for the biological activity of the protein or by employing assays that are independent of such activity, such as western blotting or radioimmunoassay using antibodies that are capable of reacting with the protein. Sambrook et al., Molecular Cloning: A Laboratory Manual, pp. 18.1-18.88 (Cold Spring Harbor Laboratory Press, 1989).

The term "hybridoma" as used herein refers to a cell created by fusion of an immortalized cell derived from an immunologic source and an antibody-producing cell. The resulting hybridoma is an immortalized cell that produces antibodies. The individual cells used to create the hybridoma can be from any mammalian source, including, but not limited to, rat, pig, rabbit, sheep, pig, goat, and human. The term also encompasses trioma cell lines, which result when progeny of heterohybrid myeloma fusions, which are the product of a fusion between human cells and a murine myeloma cell line, are subsequently fused with a plasma cell. Furthermore, the term is meant to include any immortalized hybrid cell line that produces antibodies such as, for example, quadromas (See, e.g., Milstein et al., *Nature*, 537:3053 (1983)).

The terms "medium", "cell culture medium", "culture medium", and "growth medium" as used herein refer to a solution containing nutrients which nourish growing eukaryotic cells. Typically, these solutions provide essential and non-essential amino acids, vitamins, energy sources, lipids, and trace elements required by the cell for minimal growth and/or survival. The solution can also contain components that enhance growth and/or survival above the minimal rate, including hormones and growth factors. The solution is formulated to a pH and salt concentration optimal for cell survival and proliferation. The medium can also be a "defined medium" or "chemically defined medium"-a serum-free medium that contains no proteins, hydrolysates or components of unknown composition. Defined media are free of animal-derived components and all components have a known chemical structure. One of skill in the art understands a defined medium can comprise recombinant polypeptides or proteins, for example, but not limited to, hormones, cytokines, interleukins and other signaling molecules.

The cell culture medium is generally "serum free" when the medium is essentially free of serum from any mammalian source (e.g. fetal bovine serum (FBS)). By "essentially free" is meant that the cell culture medium comprises between about 0-5% serum, preferably between about 0-1% serum, and most preferably between about 0-0.1% serum. Advantageously, serum-free "defined" medium can be used, wherein the identity and concentration of each of the components in the medium is known (i.e., an undefined component such as bovine pituitary extract (BPE) is not present in the culture medium).

When used herein, the term "glutamine" refers to the amino acid L-glutamine (also known as "Gln" and "Q" by three-letter and single-letter designation, respectively) which is recognized as both an amino acid building block for protein synthesis and as an energy source in cell culture. Thus, the terms "glutamine" and "L-glutamine" are used interchangeably herein.

The term "glucose" refers to either of α-D-glucose or β-D-glucose, separately or in combination. It is noted that α and β glucose forms are interconvertible in solution.

The term "osmolality" is a measure of the osmotic pressure of dissolved solute particles in an aqueous solution. The solute particles include both ions and non-ionized molecules. Osmolality is expressed as the concentration of osmotically active particles (i.e., osmoles) dissolved in 1 kg of water (1 mOsm/kg $H_2O$ at 38° C. is equivalent to an osmotic pressure of 19 mm Hg). "Osmolarity" refers to the number of solute particles dissolved in 1 liter of solution. Solutes which can be added to the culture medium so as to increase the osmolality thereof include proteins, peptides, amino acids, non-metabolized polymers, vitamins, ions, salts, sugars, metabolites, organic acids, lipids, etc. In the preferred embodiment, the concentration of amino acids and NaCl in the culture medium is increased in order to achieve the desired osmolality ranges set forth herein. When used herein, the abbreviation "mOsm" means "milliosmoles/kg $H_2O$".

The term "cell viability" as used herein refers to the ability of cells in culture to survive under a given set of culture conditions or experimental variations. The term as used herein also refers to that portion of cells which are alive at a particular time in relation to the total number of cells, living and dead, in the culture at that time.

The term "perfusion culture" as used herein refers to a method of culturing cells in which additional components are provided continuously or semi-continuously to the culture subsequent to the beginning of the culture process. The provided components typically comprise nutritional supplements for the cells which have been depleted during the culturing process. A portion of the cells and/or components in the medium are typically harvested on a continuous or semi-continuous basis and are optionally purified.

The terms "polypeptide" or "protein" as used herein refers a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. If a single polypeptide is the discrete functioning unit and does require permanent physical association with other polypeptides in order to form the discrete functioning unit, the terms "polypeptide" and "protein" as used herein are used interchangeably. If discrete functional unit is comprised of more than one polypeptide that physically associate with one another, the term "protein" as used herein refers to the multiple polypeptides that are physically coupled and function together as the discrete unit.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

"Recombinantly expressed polypeptide" and "recombinant polypeptide" as used herein refer to a polypeptide expressed from a host cell that has been genetically engineered to express that polypeptide. The recombinantly expressed polypeptide can be identical or similar to polypeptides that are normally expressed in the mammalian host cell. The recombinantly expressed polypeptide can also foreign to the host cell, i.e. heterologous to peptides normally expressed in the mammalian host cell. Alternatively, the recombinantly expressed polypeptide can be chimeric in that portions of the polypeptide contain amino acid sequences that are identical or similar to polypeptides normally expressed in the mammalian host cell, while other portions are foreign to the host cell. As used herein, the terms "recombinantly expressed polypeptide" and "recombinant polypeptide" also encompasses an antibody produced by a hybridoma.

The term "seeding" as used herein refers to the process of providing a cell culture to a bioreactor or another vessel. In one embodiment, the cells have been propagated previously in another bioreactor or vessel. In another embodiment, the cells have been frozen and thawed immediately prior to providing them to the bioreactor or vessel. The term refers to any number of cells, including a single cell.

The term "titer" as used herein refers to the total amount of recombinantly expressed polypeptide or protein produced by a cell culture divided by a given amount of medium volume. Titer is typically expressed in units of milligrams of polypeptide or protein per milliliter of medium or in units of grams of polypeptide or protein per liter of medium.

As used in the present disclosure and claims, the singular forms "a", "an", and "the" include plural forms unless the context clearly dictates otherwise.

It is understood that whenever embodiments are described herein with the language "comprising" otherwise analogous embodiments described in terms of "consisting" and/or "consisting essentially of" are also provided.

II. Cell Culture Medium and Methods of Using Thereof

The present invention relates to cell culture media and methods of use thereof. The media of the invention reduces decreases in cellular viability and specific productivity associated with growth of mammalian cells in glutamine-free growth medium. A medium according to the invention can be used in a batch culture, fed-batch culture or a perfusion culture. In one embodiment, a medium of the invention is a basal medium. In another embodiment, a medium of the invention is a feed medium.

In one embodiment, a medium according to the present invention comprises nucleic acid synthesis precursors. A medium can comprise sufficient amount of hypoxanthine and thymidine such that the hypoxanthine concentration in the culture by between about 20 and about 1000 µM, and the thymidine concentration between about 2 and about 1000 µM. In one embodiment, the medium described herein comprises a hypoxanthine concentration between about 10 µM and about 1000 µM, about 10 µM and about 900 µM, about 10 µM and about 800 µM, about 10 µM and about 700 µM, about 10 µM and about 600 µM, about 10 µM and about 500 µM, about 10 µM and about 400 µM, about 10 µM and about 300 µM, about 10 µM and about 200 µM, about 10 µM and about 150 µM, about 10 µM and about 100 µM, about 10 µM and about 50 µM, about 10 µM and about 25 µM, about 20 µM and about 1000 µM, about 20 µM and about 900 µM, about 20 µM and about 800 µM, about 20 µM and about 700 µM, about 20 µM and about 600 µM, about 20 µM and about 500 µM, about 20 µM and about 400 µM, about 20 µM and about 300 µM, about 20 µM and about 200 µM, about 20 µM and about 150 µM, about 20 µM and about 100 µM, about 20 µM and about 50 µM, about 25 µM and about 1000 µM, about 25 µM and about 900 µM, about 25 µM and about 800 µM, about 25 µM and about 700 µM, about 25 µM and about 600 µM, about 25 µM and about 500 µM, about 25 µM and about 400 µM, about 25 µM and about 300 µM, about 25 µM and about 200 µM, about 25 µM and about 150 µM, about 25 µM and about 100 µM, about 25 µM and about 50 µM, about 50 µM and about 1000 µM, about 50 µM and about 900 µM, about 50 µM and about 800 µM, about 50 µM and about 700 µM, about 50 µM and about 600 µM, about 50 µM and about 500 µM, about 50 µM and about 400 µM, about 50 µM and about 300 µM, about 50 µM and about 200 µM, about 50 µM and about 150 µM, about 50 µM and about 100 µM, about 75 µM and about 1000 µM, about 75 µM and about 900 µM, about 75 µM and about 800 µM, about 75 µM and about 700 µM, about 75 µM and about 600 µM, about 75 µM and about 500 µM, about 75 µM and about 400 µM, about 75 µM and about 300 µM, about 75 µM and about 200 µM, about 75 µM and about 150 µM, or about 75 µM and about 100 µM, and a thymidine concentration of between about 1 µM and about 1000 µM, about 1 µM and about 900 µM, about 1 µM and about 800 µM, about 1 µM and about 700 µM, about 1 µM and about 600 µM, about 1 µM and about 500 µM, about 1 µM and about 400 µM, about 1 µM and about 300 µM, about 1 µM and about 200 µM, about 1 µM and about 150 µM, about 1 µM and about 100 µM, about 1 μM and about 50 μM, about 1 μM and about 45 μM, about 1 μM and about 40 μM, about 1 μM and about 35 μM, about 1 μM and about 30 μM, about 1 μM and about 25 μM, about 1 μM and about 20 μM, about 1 μM and about 15 μM, about 1 μM and about 10 μM, about 1 μM and about 5 μM, about 2 μM and about 1000 μM, about 2 μM and about 900 μM, about 2 μM and about 800 μM, about 2 μM and about 700 μM, about 2 μM and about 600 μM, about 2 μM and about 500 μM, about 2 μM and about 400 μM, about 2 μM and about 300 μM, about 2 μM and about 200 μM, about 2 μM and about 150 μM, about 2 μM and about 100 μM, about 2 μM and about 50 μM, about 2 μM and about 45 μM, about 2 μM and about 40 μM, about 2 μM and about 35 μM, about 2 μM and about 30 μM, about 2 μM and about 25 μM, about 2 μM and about 20 μM, about 2 μM and about 15 μM, about 2 μM and about 10 μM, about 2 μM and about 5 μM, about 5 μM and about 1000 μM, about 5 μM and about 900 μM, about 5 μM and about 800 μM, about 5 μM and about 700 μM, about 5 μM and about 600 μM, about 5 μM and about 500 μM, about 5 μM and about 400 μM, about 5 μM and about 300 μM, about 5 μM and about 200 μM, about 5 μM and about 150 μM, about 5 μM and about 100 μM, about 5 μM and about 50 μM, about 5 μM and about 45 μM, about 5 μM and about 40 μM, about 5 μM and about 35 μM, about 5 μM and about 30 μM, about 5 μM and about 25 μM, about 5 μM and about 20 μM, about 5 μM and about 15 μM, about 5 μM and about 10 μM, about 10 μM and about 1000 μM, about 10 μM and about 900 μM, about 10 μM and about 800 μM, about 10 μM and about 700 μM, about 10 μM and about 600 μM, about 10 μM and about 500 μM, about 10 μM and about 400 μM, about 10 μM and about 300 μM, about 10 μM and about 200 μM, about 10 μM and about 150 μM, about 10 μM and about 100 μM, about 10 μM and about 50 μM, about 10 μM and about 45 μM, about 10 μM and about 40 μM, about 10 μM and about 35 μM, about 10 μM and about 30 μM, about 10 μM and about 25 μM, or about 10 μM and about 20 μM. In one embodiment, the medium comprises about 100 μM hypoxanthine and about 16 μM thymidine.

In another embodiment, a feed medium described herein comprises a sufficient amount of hypoxanthine and thymidine to raise the hypoxanthine concentration in the culture to between about 20 and about 1000 μM, and the thymidine concentration between about 2 and about 1000 μM. In one embodiment, the feed medium described herein raises the hypoxanthine concentration to between about 10 μM and about 1000 μM, about 10 μM and about 900 μM, about 10 μM and about 800 μM, about 10 μM and about 700 μM, about 10 μM and about 600 μM, about 10 μM and about 500 μM, about 10 μM and about 400 μM, about 10 μM and about 300 μM, about 10 μM and about 200 μM, about 10 μM and about 150 μM, about 10 μM and about 100 μM, about 10 μM and about 50 μM, about 10 μM and about 25 μM, about 20 μM and about 1000 μM, about 20 μM and about 900 μM, about 20 μM and about 800 μM, about 20 μM and about 700 μM, about 20 μM and about 600 μM, about 20 μM and about 500 μM, about 20 μM and about 400 μM, about 20 μM and about 300 μM, about 20 μM and about 200 μM, about 20 μM and about 150 μM, about 20 μM and about 100 μM, about 20 μM and about 50 μM, about 25 μM and about 1000 μM, about 25 μM and about 900 μM, about 25 μM and about 800 μM, about 25 μM and about 700 μM, about 25 μM and about 600 μM, about 25 μM and about 500 μM, about 25 μM and about 400 μM, about 25 μM and about 300 μM, about 25 μM and about 200 μM, about 25 μM and about 150 μM, about 25 μM and about 100 μM, about 25 μM and about 50 μM, about 50 μM and about 1000 μM, about 50 μM and about 900 μM, about 50 μM and about 800 μM, about 50 μM and about 700 μM, about 50 μM and about 600 μM, about 50 μM and about 500 μM, about 50 μM and about 400 μM, about 50 μM and about 300 μM, about 50 μM and about 200 μM, about 50 μM and about 150 μM, about 50 μM and about 100 μM, about 75 μM and about 1000 μM, about 75 μM and about 900 μM, about 75 μM and about 800 μM, about 75 μM and about 700 μM, about 75 μM and about 600 μM, about 75 μM and about 500 μM, about 75 μM and about 400 μM, about 75 μM and about 300 μM, about 75 μM and about 200 μM, about 75 μM and about 150 μM, or about 75 μM and about 100 μM, and the thymidine concentration to between about 1 μM and about 1000 μM, about 1 μM and about 900 μM, about 1 μM and about 800 μM, about 1 μM and about 700 μM, about 1 μM and about 600 μM, about 1 μM and about 500 μM, about 1 μM and about 400 μM, about 1 μM and about 300 μM, about 1 μM and about 200 μM, about 1 μM and about 150 μM, about 1 μM and about 100 μM, about 1 μM and about 50 μM, about 1 μM and about 45 μM, about 1 μM and about 40 μM, about 1 μM and about 35 μM, about 1 μM and about 30 μM, about 1 μM and about 25 μM, about 1 μM and about 20 μM, about 1 μM and about 15 μM, about 1 μM and about 10 μM, about 1 μM and about 5 μM, about 2 μM and about 1000 μM, about 2 μM and about 900 μM, about 2 μM and about 800 μM, about 2 μM and about 700 μM, about 2 μM and about 600 μM, about 2 μM and about 500 μM, about 2 μM and about 400 μM, about 2 μM and about 300 μM, about 2 μM and about 200 μM, about 2 μM and about 150 μM, about 2 μM and about 100 μM, about 2 μM and about 50 μM, about 2 μM and about 45 μM, about 2 μM and about 40 μM, about 2 μM and about 35 μM, about 2 μM and about 30 μM, about 2 μM and about 25 μM, about 2 μM and about 20 μM, about 2 μM and about 15 μM, about 2 μM and about 10 μM, about 2 μM and about 5 μM, about 5 μM and about 1000 μM, about 5 μM and about 900 μM, about 5 μM and about 800 μM, about 5 μM and about 700 μM, about 5 μM and about 600 μM, about 5 μM and about 500 μM, about 5 μM and about 400 μM, about 5 μM and about 300 μM, about 5 μM and about 200 μM, about 5 μM and about 150 μM, about 5 μM and about 100 μM, about 5 μM and about 50 μM, about 5 μM and about 45 μM, about 5 μM and about 40 μM, about 5 μM and about 35 μM, about 5 μM and about 30 μM, about 5 μM and about 25 μM, about 5 μM and about 20 μM, about 5 μM and about 15 μM, about 5 μM and about 10 μM, about 10 μM and about 1000 μM, about 10 μM and about 900 μM, about 10 μM and about 800 μM, about 10 μM and about 700 μM, about 10 μM and about 600 μM, about 10 μM and about 500 μM, about 10 μM and about 400 μM, about 10 μM and about 300 μM, about 10 μM and about 200 μM, about 10 μM and about 150 μM, about 10 μM and about 100 μM, about 10 μM and about 50 μM, about 10 μM and about 45 μM, about 10 μM and about 40 μM, about 10 μM and about 35 μM, about 10 μM and about 30 μM, about 10 μM and about 25 μM, or about 10 μM and about 20 μM. A skilled artisan readily understands that the absolute amount of hypoxanthine and thymidine supplemented by a feed medium to a cell culture can be calculated from the volume of feed medium added to the culture and the hypoxanthine and thymidine concentration of the feed medium.

In one embodiment, a medium according to the present invention comprises adenosine. A medium can comprise sufficient amount of adenosine such that the adenosine concentration in the culture is between 10 to 1000 μM. In one embodiment, the medium described herein comprises an adenosine concentration between about 10 μM and about 1000 μM, about 10 μM and about 900 μM, about 10 μM and about 800 μM, about 10 μM and about 700 μM, about 10 μM and about 600 µM, about 10 µM and about 500 µM, about 10 µM and about 400 µM, about 10 µM and about 300 µM, about 10 µM and about 200 µM, about 10 µM and about 150 µM, about 10 µM and about 100 µM, about 10 µM and about 50 µM, about 10 µM and about 25 µM, about 25 µM and about 1000 µM, about 25 µM and about 900 µM, about 25 µM and about 800 µM, about 25 µM and about 700 µM, about 25 µM and about 600 µM, about 25 µM and about 500 µM, about 25 µM and about 400 µM, about 25 µM and about 300 µM, about 25 µM and about 200 µM, about 25 µM and about 150 µM, about 25 µM and about 100 µM, about 25 µM and about 50 µM, about 50 µM and about 1000 µM, about 50 µM and about 900 µM, about 50 µM and about 800 µM, about 50 µM and about 700 µM, about 50 µM and about 600 µM, about 50 µM and about 500 µM, about 50 µM and about 400 µM, about 50 µM and about 300 µM, about 50 µM and about 200 µM, about 50 µM and about 150 µM, about 50 µM and about 100 µM, about 75 µM and about 1000 µM, about 75 µM and about 900 µM, about 75 µM and about 800 µM, about 75 µM and about 700 µM, about 75 µM and about 600 µM, about 75 µM and about 500 µM, about 75 µM and about 400 µM, about 75 µM and about 300 µM, about 75 µM and about 200 µM, about 75 µM and about 150 µM, or about 75 µM and about 100 µM. In one embodiment, the medium comprises about 100 µM adenosine. In another embodiment, the medium comprises about 500 µM adenosine.

In another embodiment, a feed medium described herein comprises a sufficient amount of adenosine to raise the adenosine concentration in the culture to between 10 to 1000 µM. In one embodiment, the feed medium described herein raises the adenosine concentration to between about 10 µM and about 1000 µM, about 10 µM and about 900 µM, about 10 µM and about 800 µM, about 10 µM and about 700 µM, about 10 µM and about 600 µM, about 10 µM and about 500 µM, about 10 µM and about 400 µM, about 10 µM and about 300 µM, about 10 µM and about 200 µM, about 10 µM and about 150 µM, about 10 µM and about 100 µM, about 10 µM and about 50 µM, about 10 µM and about 25 µM, about 25 µM and about 1000 µM, about 25 µM and about 900 µM, about 25 µM and about 800 µM, about 25 µM and about 700 µM, about 25 µM and about 600 µM, about 25 µM and about 500 µM, about 25 µM and about 400 µM, about 25 µM and about 300 µM, about 25 µM and about 200 µM, about 25 µM and about 150 µM, about 25 µM and about 100 µM, about 25 µM and about 50 µM, about 50 µM and about 1000 µM, about 50 µM and about 900 µM, about 50 µM and about 800 µM, about 50 µM and about 700 µM, about 50 µM and about 600 µM, about 50 µM and about 500 µM, about 50 µM and about 400 µM, about 50 µM and about 300 µM, about 50 µM and about 200 µM, about 50 µM and about 150 µM, about 50 µM and about 100 µM, about 75 µM and about 1000 µM, about 75 µM and about 900 µM, about 75 µM and about 800 µM, about 75 µM and about 700 µM, about 75 µM and about 600 µM, about 75 µM and about 500 µM, about 75 µM and about 400 µM, about 75 µM and about 300 µM, about 75 µM and about 200 µM, about 75 µM and about 150 µM, or about 75 µM and about 100 µM. A skilled artisan readily understands that the absolute amount of hypoxanthine and thymidine supplemented by a feed medium to a cell culture can be calculated from the volume of feed medium added to the culture and the hypoxanthine and thymidine concentration of the feed medium.

In one embodiment, a medium according to the present invention comprises between about 0.5 µM and about 500 µM of at least one corticosteroid. In one embodiment, the corticosteroid is dexamethasone, hydrocortisone, or prednisolone. In one embodiment, the medium comprises at least one corticosteroid at a concentration of between about 0.5 µM and about 500 µM, about 0.5 µM and about 450 µM, about 0.5 µM and about 400 µM, about 0.5 µM and about 350 µM, about 0.5 µM and about 300 µM, about 0.5 µM and about 250 µM, about 0.5 µM and about 200 µM, about 0.5 µM and about 150 µM, about 0.5 µM and about 100 µM, about 0.5 µM and about 50 µM, about 0.5 µM and about 40 µM, about 0.5 µM and about 30 µM, about 0.5 µM and about 20 µM, about 0.5 µM and about 10 µM, about 0.5 µM and about 5 µM, about 1 µM and about 5 µM, or about 1 µM and about 3 µM.

In another embodiment, a feed medium described herein comprises a sufficient amount of at least one corticosteroid to raise the corticosteroid concentration in the culture to between about 0.5 µM and about 500 µM, about 0.5 µM and about 450 µM, about 0.5 µM and about 400 µM, about 0.5 µM and about 350 µM, about 0.5 µM and about 300 µM, about 0.5 µM and about 250 µM, about 0.5 µM and about 150 µM, about 0.5 µM and about 100 µM, about 0.5 µM and about 50 µM, about 0.5 µM and about 40 µM, about 0.5 µM and about 30 µM, about 0.5 µM and about 20 µM, about 0.5 µM and about 10 µM, about 0.5 µM and about 5 µM, about 1 µM and about 5 µM, or about 1 µM and about 3 µM. In one embodiment, the corticosteroid concentration in the medium raises the corticosteroid concentration to about 2.5 µM. In another embodiment, the corticosteroid concentration in the medium raises the corticosteroid concentration to about 25 µM.

In one embodiment, a medium described herein is a serum-free medium, animal protein-free medium or a chemically-defined medium. In a specific embodiment, a medium described herein is a chemically-defined medium.

The present invention further provides a cell culture composition comprising a medium described herein and cells.

In one embodiment, a cell culture composition according to the invention can be a batch culture, fed-batch culture or a perfusion culture. In a specific embodiment, a cell culture composition of the invention is a fed batch culture.

In one embodiment, a cell culture composition described herein comprises mammalian cells selected from the group consisting of CHO cells, HEK cells, NSO cells, PER.C6 cells, 293 cells, HeLa cells, and MDCK cells. In a specific embodiment, a cell culture composition described herein comprises CHO cells. In another specific embodiment, a cell culture composition described herein comprises HEK cells. In another specific embodiment, a cell culture composition described herein comprises hybridoma cells.

A cell culture composition described herein can comprise cells that have been adapted to grow in serum free medium, animal protein free medium or chemically defined medium. Or it can comprise cells that have been genetically modified to increase their life-span in culture. In one embodiment, the cells have been modified to express an anti-apoptotic gene. In a specific embodiment, the cells have been modified to express the bcl-xL antiapoptotic gene. Additional anti-apoptotic genes that can be used in accordance with the present invention include, but are not limited to, E1B-9K, Aven, Mcl.

The present invention provides a method of culturing cells, comprising contacting the cells with a medium disclosed herein.

Cell cultures can be cultured in a batch culture, fed batch culture or a perfusion culture. In one embodiment, a cell culture according to a method of the present invention is a batch culture. In another embodiment, a cell culture according to a method of the present invention is a fed batch culture. In a further embodiment, a cell culture according to a method of the present invention is a perfusion culture.

In one embodiment, a cell culture according to a method of the present invention is a serum-free culture. In another embodiment, a cell culture according to a method of the present invention is a chemically defined culture. In a further embodiment, a cell culture according to a method of the present invention is an animal protein free culture.

In one embodiment, a cell culture is contacted with a medium described herein during the growth phase of the culture. In another embodiment, a cell culture is contacted with a medium described herein during the production phase of the culture.

In one embodiment, a cell culture according to the invention is contacted with a feed medium described herein during the production phase of the culture. In one embodiment, the culture is supplemented with the feed medium between about 1 and about 25 times during the second time period. In another embodiment, a culture is supplemented with the feed medium between about 1 and about 20 times, between about 1 and about 15 times, or between about 1 and about 10 times during the first time period. In a further embodiment, a culture is supplemented with the feed medium at least once, at least twice, at least three times, at least four times, at least five times, at least 6 times, at least 7 times, at least 8 times, at least 9 times, at least 10 times, at least 1 times, at least 12 times, at least 13 times, at least 14 times, at least 15 times, at least 20 times, at least 25 times. In a specific embodiment, the culture is a fed batch culture. In another specific embodiment, the culture is a perfusion culture.

A culture according to the invention can be contacted with a feed medium described herein at regular intervals. In one embodiment, the regular interval is about once a day, about once every two days, about once every three days, about once every 4 days, or about once every 5 days. In a specific embodiment, the culture is a fed batch culture. In another specific embodiment, the culture is a perfusion culture.

A culture according to the invention can be contacted with a feed medium described herein on an as needed basis based on the metabolic status of the culture. In one embodiment, a metabolic marker of a fed batch culture is measured prior to supplementing the culture with a feed medium described herein. In one embodiment, the metabolic marker is selected from the group consisting of: lactate concentration, ammonium concentration, alanine concentration, glutamine concentration, glutamate concentration, cell specific lactate production rate to the cell specific glucose uptake rate ratio (LPR/GUR ratio), and Rhodamine 123 specific cell fluorescence. In one embodiment, an LPR/GUR value of >0.1 indicates the need to supplement the culture with a feed medium described herein. In a further specific embodiment, a lactate concentration of >3 g/L indicates the need to supplement the culture with a feed medium described herein. In another embodiment, a culture according to the present invention is supplemented with a feed medium described herein when the LPR/GUR value of the culture is >0.1 or when the lactate concentration of the culture is >3 g/L. In a specific embodiment, the culture is a fed batch culture. In another specific embodiment, the culture is a perfusion culture.

In one embodiment, a medium described herein is a feed medium for a fed batch cell culture. A skilled artisan understands that a fed batch cell culture can be contacted with a feed medium more than once. In one embodiment, a fed batch cell culture is contacted with a medium described herein only once. In another embodiment, a fed batch cell culture is contacted with a medium described herein more than once, for example, at least twice, at least three times, at least four times, at least five times, at least six times, at least seven times, or at least ten times.

In accordance with the present invention, the total volume of feed medium added to a cell culture should optimally be kept to a minimal amount. For example, the total volume of the feed medium added to the cell culture can be 1, 2, 3, 4, 5, 6, 7, 8, 9, 10, 15, 20, 25, 30, 35, 40, 45 or 50% of the volume of the cell culture prior to adding the feed medium.

Cell cultures can be grown to achieve a particular cell density, depending on the needs of the practitioner and the requirement of the cells themselves, prior to being contacted with a medium described herein. In one embodiment, the cell culture is contacted with a medium described herein at a viable cell density of 1, 5, 10, 15, 20, 25, 30, 35, 40, 45, 50, 55, 60, 65, 70, 75, 80, 85, 90, 95 or 99 percent of maximal viable cell density. In a specific embodiment, the medium is a feed medium.

Cell cultures can be allowed to grow for a defined period of time before they are contacted with a medium described herein. In one embodiment, the cell culture is contacted with a medium described herein at day 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the cell culture. In another embodiment, the cell culture is contacted with a medium described herein at week 1, 2, 3, 4, 5, 6, 7, or 8 of the cell culture. In a specific embodiment, the medium is a feed medium.

Cell cultures can be cultured in the production phase for a defined period of time. In one embodiment, the cell culture is contacted with a feed medium described herein at day 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 of the production phase.

In certain embodiments, the cellular viability of cells in a culture media according to the invention is increased by about 2%, about 3%, about 4%, about 5%, about 6%, about 7%, about 8%, about 9%, about 10%, about 15%, about 20%, about 25%, about 30%, about 35%, or about 40% compared to cell viability of cells in unsupplemented glutamine-free media.

A culture according to the invention can be maintained in production phase for between about 1 day and about 120 days. In one embodiment, a culture is maintained in production phase for between about 1 day and about 120 days, about 1 day and about 115 days, about 1 day and about 110 days, about 1 day and about 105 days, about 1 day and about 100 days, about 1 day and about 95 days, about 1 day and about 90 days, about 1 day and about 85 days, about 1 day and about 80 days, about 1 day and about 75 days, about 1 day and about 70 days, about 1 day and about 65 days, about 1 day and about 60 days, about 1 day and about 55 days, about 1 day and about 50 days, about 1 day and about 45 days, about 1 day and about 40 days, about 1 day and about 35 days, about 1 day and about 30 days, about 1 day and about 30 days, about 1 day and about 25 days, about 1 day and about 20 days, about 1 day and about 15 days, about 1 day and about 14 days, about 1 day and about 13 days, about 1 day and about 12 days, about 1 day and about 11 days, about 1 day and about 10 days, about 1 day and about 9 days, about 1 day and about 8 days, about 1 day and about 7 days, about 1 day and about 6 days, about 1 day and about 5 days, about 1 day and about 4 days, about 1 day and about 3 days, about 2 days and about 25 days, about 3 days and about 25 days, about 4 days and about 25 days, about 5 days and about 25 days, about 6 days and about 25 days, about 7 days and about 25 days, about 8 days and about 25 days, about 9 days and about 25 days, about 10 days and about 25 days, about 15 days and about 25 days, about 20 days and about 25 days, about 2 days and about 30 days, about 3 days and about 30 days, about 4 days and about 30 days, about 5 days and about 30 days, about 6 days and about 30 days, about 7 days and about 30 days, about 8 days and about 30 days, about 9 days and about 30 days, about 10 days and about 30 days, about 15 days and about 30 days, about 20 days and about 30 days, about 25 days and about 30 days, about 2 days and about 50 days, about 3 days and about 50 days, about 4 days and about 50 days, about 5 days and about 50 days, about 6 days and about 50 days, about 7 days and about 50 days, about 8 days and about 50 days, about 9 days and about 50 days, about 10 days and about 50 days, about 15 days and about 50 days, about 20 days and about 50 days, about 25 days and about 50 days, about 30 days and about 50 days, about 40 days and about 50 days, about 2 days and about 75 days, about 3 days and about 75 days, about 4 days and about 75 days, about 5 days and about 75 days, about 6 days and about 75 days, about 7 days and about 75 days, about 8 days and about 75 days, about 9 days and about 75 days, about 10 days and about 75 days, about 15 days and about 75 days, about 20 days and about 75 days, about 25 days and about 75 days, about 30 days and about 75 days, about 40 days and about 75 days, about 50 days and about 75 days, about 2 days and about 100 days, about 3 days and about 100 days, about 4 days and about 100 days, about 5 days and about 100 days, about 6 days and about 100 days, about 7 days and about 100 days, about 8 days and about 100 days, about 9 days and about 100 days, about 10 days and about 100 days, about 15 days and about 100 days, about 20 days and about 100 days, about 25 days and about 100 days, about 30 days and about 100 days, about 40 days and about 100 days, about 50 days and about 100 days, about 75 days and about 100 days, about 2 days and about 120 days, about 3 days and about 120 days, about 4 days and about 120 days, about 5 days and about 120 days, about 6 days and about 120 days, about 7 days and about 120 days, about 8 days and about 120 days, about 9 days and about 120 days, about 10 days and about 120 days, about 15 days and about 120 days, about 20 days and about 120 days, about 25 days and about 120 days, about 30 days and about 120 days, about 40 days and about 120 days, about 50 days and about 120 days, about 75 days and about 120 days, or about 100 days and about 120 days. In another embodiment, a culture is maintained in production phase for at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 15 days, at least about 20 days, at least about 25 days, at least about 30 days, at least about 35 days, at least about 40 days, at least about 45 days, at least about 50 days, at least about 55 days, at least about 60 days, at least about 65 days, at least about 70 days, at least about 75 days, at least about 80 days, at least about 85 days, at least about 90 days, at least about 95 days, at least about 100 days, at least about 105 days, at least about 110 days, at least about 115 days, or at least about 120 days. In a further embodiment, a culture is maintained in production phase for about 1 day, about 2 days, about 3 days, about 4 days, about 5 days, about 6 days, about 7 days, about 8 days, about 9 days, about 10 days, about 11 days, about 12 days, about 15 days, about 20 days, about 25 days, about 30 days, about 35 days, about 40 days, about 45 days, about 50 days, about 55 days, about 60 days, about 65 days, about 70 days, about 75 days, about 80 days, about 85 days, about 90 days, about 95 days, about 100 days, about 105 days, about 110 days, about 115 days, or about 120 days.

The present invention further provides a method of producing a protein or polypeptide of interest, comprising culturing cells capable of producing the protein or polypeptide of interest in a culture comprising a medium described herein; and isolating the protein or polypeptide from the culture. In one embodiment, the protein or polypeptide of interest is a recombinant protein or polypeptide. In one embodiment, the protein or polypeptide of interest is an enzyme, receptor, antibody, immunoadhesin, hormone, regulatory factor, antigen, or binding agent. In a specific embodiment, the protein is an antibody. In another embodiment, the protein is an immunoadhesin.

In one embodiment of the present invention, a cell culture comprising a medium described herein can be maintained in production phase longer than a cell culture that does not comprise exogenous nucleic acid precursors or corticosteroids. A skilled artisan readily understands that an extended production phase can lead to an increase in the total amount of polypeptide produce by the cell culture. In one embodiment, a method of producing a polypeptide of interest according to the present invention produces more polypeptide than the amount produced by a method that does not comprise maintaining cells capable of producing the polypeptide in a culture comprising exogenous nucleic acid precursors or corticosteroids. In one embodiment, a method according to the present invention produces between about 5% and about 500%, about 5% and about 250%, about 5% and about 100%, about 5% and about 80%, about 5% and about 50%, about 5% and about 30%, about 10% and about 500%, about 20% and about 500%, about 30% and about 500%, about 50% and about 500%, or about 100% and about 500% more protein or polypeptide. In another embodiment, a method according to the present invention produces at least about 5%, at least about 10%, at least about 15%, at least about 20%, at least about 25%, at least about 30%, at least about 40%, at least about 50%, at least about 70%, at least about 90%, or at least about 100% more protein or polypeptide. In another embodiment, a method according to the present invention produces at least about 2 times, three times, four times, five times or ten times more protein or polypeptide. In a specific embodiment, the protein or polypeptide is an antibody or immunoadhesin.

In one embodiment, a method of producing a polypeptide of interest according to the present invention produces a higher titer of the polypeptide in the cell culture than the titer produced by a method that does not comprise maintaining the cells in a culture comprising nucleic acid precursors or corticosteroids. In one embodiment, a method according to the present invention produces between about 5% and about 500%, about 5% and about 250%, about 5% and about 100%, about 5% and about 80%, about 5% and about 50%, about 5% and about 30%, about 10% and about 500%, about 20% and about 500%, about 30% and about 500%, about 50% and about 500%, or about 100% and about 500% higher titer. In another embodiment, a method according to the present invention produces at least about 5%, at least about 10%, at least about 15%, at least about 20%, at least about 25%, at least about 30%, at least about 40%, at least about 50%, at least about 70%, at least about 90%, or at least about 100% higher titer. In another embodiment, a method according to the present invention produces at least about 2 times, three times, four times, five times or ten times higher titer. In a specific embodiment, the protein or polypeptide is an antibody.

In a specific embodiment, a method of producing a polypeptide of interest according to the present invention produces a maximum protein or polypeptide titer of at least about 2 g/liter, at least about 2.5 g/liter, at least about 3 g/liter, at least about 3.5 g/liter, at least about 4 g/liter, at least about 4.5 g/liter, at least about 5 g/liter, at least about 6 g/liter, at least about 7 g/liter, at least about 8 g/liter, at least about 9 g/liter, or at least about 10 g/liter. In another embodiment, the method according to the present invention produces a maximum protein or polypeptide titer of between about 1 g/liter and about 10 g/liter, about 1.5 g/liter and about 10 g/liter, about 2 g/liter and about 10 g/liter, about 2.5 g/liter and about 10 g/liter, about 3 g/liter and about 10 g/liter, about 4 g/liter and about 10 g/liter, about 5 g/liter and about 10 g/liter, about 1 g/liter and about 5 g/liter, about 1 g/liter and about 4.5 g/liter, or about 1 g/liter and about 4 g/liter. In a specific embodiment, the protein or polypeptide is an antibody. In another embodiment, the protein or polypeptide is a blood clotting factor.

The invention further provides a conditioned cell culture medium produced by a method described herein.

In one embodiment, a conditioned cell culture medium according to the invention comprises a recombinant protein or polypeptide. In a specific embodiment, a conditioned cell culture medium according to the invention comprises a recombinant protein or polypeptide at a titer of at least about 2 g/liter, at least about 2.5 g/liter, at least about 3 g/liter, at least about 3.5 g/liter, at least about 4 g/liter, at least about 4.5 g/liter, at least about 5 g/liter, at least about 6 g/liter, at least about 7 g/liter, at least about 8 g/liter, at least about 9 g/liter, or at least about 10 g/liter, or a titer of between about 1 g/liter and about 10 g/liter, about 1.5 g/liter and about 10 g/liter, about 2 g/liter and about 10 g/liter, about 2.5 g/liter and about 10 g/liter, about 3 g/liter and about 10 g/liter, about 4 g/liter and about 10 g/liter, about 5 g/liter and about 10 g/liter, about 1 g/liter and about 5 g/liter, about 1 g/liter and about 4.5 g/liter, or about 1 g/liter and about 4 g/liter. In another embodiment, a conditioned cell culture medium according to the invention comprises a recombinant protein or polypeptide at a higher titer than the titer obtained without the use of a medium described herein. In a specific embodiment, the protein or polypeptide is an antibody.

Polypeptides

Any polypeptide that is expressible in a host cell can be produced in accordance with the present invention. The polypeptide can be expressed from a gene that is endogenous to the host cell, or from a gene that is introduced into the host cell through genetic engineering. The polypeptide can be one that occurs in nature, or can alternatively have a sequence that was engineered or selected by the hand of man. An engineered polypeptide can be assembled from other polypeptide segments that individually occur in nature, or can include one or more segments that are not naturally occurring.

Polypeptides that can desirably be expressed in accordance with the present invention will often be selected on the basis of an interesting biological or chemical activity. For example, the present invention can be employed to express any pharmaceutically or commercially relevant enzyme, receptor, antibody, immunoadhesin, hormone, regulatory factor, antigen, binding agent, etc.

Antibodies

Given the large number of antibodies currently in use or under investigation as pharmaceutical or other commercial agents, production of antibodies is of particular interest in accordance with the present invention. Antibodies are proteins that have the ability to specifically bind a particular antigen. Any antibody that can be expressed in a host cell can be used in accordance with the present invention. In one embodiment, the antibody to be expressed is a monoclonal antibody.

Particular antibodies can be made, for example, by preparing and expressing synthetic genes that encode the recited amino acid sequences or by mutating human germline genes to provide a gene that encodes the recited amino acid sequences. Moreover, these antibodies can be produced, e.g., using one or more of the following methods.

Numerous methods are available for obtaining antibodies, particularly human antibodies. One exemplary method includes screening protein expression libraries, e.g., phage or ribosome display libraries. Phage display is described, for example, U.S. Pat. No. 5,223,409; Smith (1985) Science 228:1315-1317; WO 92/18619; WO 91/17271; WO 92/20791; WO 92/15679; WO 93/01288; WO 92/01047; WO 92/09690; and WO 90/02809. The display of Fab's on phage is described, e.g., in U.S. Pat. Nos. 5,658,727; 5,667,988; and 5,885,793.

In addition to the use of display libraries, other methods can be used to obtain an antibody. For example, a protein or a peptide thereof can be used as an antigen in a non-human animal, e.g., a rodent, e.g., a mouse, hamster, or rat.

In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity can be produced and selected. See, e.g., XENOMOUSE™, Green et al. (1994) *Nature Genetics* 7:13-21, U.S. 2003-0070185, WO 96/34096, and WO 96/33735.

In another embodiment, a monoclonal antibody is obtained from the non-human animal, and then modified, e.g., humanized or deimmunized. Winter describes an exemplary CDR-grafting method that can be used to prepare humanized antibodies described herein (U.S. Pat. No. 5,225,539). All or some of the CDRs of a particular human antibody can be replaced with at least a portion of a non-human antibody. In one embodiment, it is only necessary to replace the CDRs required for binding or binding determinants of such CDRs to arrive at a useful humanized antibody that binds to an antigen.

Humanized antibodies can be generated by replacing sequences of the Fv variable region that are not directly involved in antigen binding with equivalent sequences from human Fv variable regions. General methods for generating humanized antibodies are provided by Morrison, S. L. (1985) *Science* 229:1202-1207, by Oi et al. (1986) *BioTechniques* 4:214, and by U.S. Pat. Nos. 5,585,089; 5,693,761; 5,693,762; 5,859,205; and 6,407,213. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, can be obtained from a hybridoma producing an antibody against a predetermined target, as described above, from germline immunoglobulin genes, or from synthetic constructs. The recombinant DNA encoding the humanized antibody can then be cloned into an appropriate expression vector. In one embodiment, the expression vector comprises a polynucleotide encoding a glutamine synthetase polypeptide. (See, e.g., Porter et al., *Biotechnol Prog* 26(5):1446-54 (2010).)

The antibody can include a human Fc region, e.g., a wild-type Fc region or an Fc region that includes one or more alterations. In one embodiment, the constant region is altered, e.g., mutated, to modify the properties of the antibody (e.g., to increase or decrease one or more of: Fc receptor binding, antibody glycosylation, the number of cysteine residues, effector cell function, or complement function). For example, the human IgG1 constant region can be mutated at one or more residues, e.g., one or more of residues 234 and 237. Antibodies can have mutations in the CH2 region of the heavy chain that reduce or alter effector function, e.g., Fc receptor binding and complement activation. For example, antibodies can have mutations such as those described in U.S. Pat. Nos. 5,624,821 and 5,648,260. Antibodies can also have mutations that stabilize the disulfide bond between the two heavy chains of an immunoglobulin, such as mutations in the hinge region of IgG4, as disclosed in the art (e.g., Angal et al. (1993) Mol. Immunol. 30:105-08). See also, e.g., U.S. 2005-0037000.

In other embodiments, the antibody can be modified to have an altered glycosylation pattern (i.e., altered from the original or native glycosylation pattern). As used in this context, "altered" means having one or more carbohydrate moieties deleted, and/or having one or more glycosylation sites added to the original antibody. Addition of glycosylation sites to the presently disclosed antibodies can be accomplished by altering the amino acid sequence to contain glycosylation site consensus sequences; such techniques are well known in the art. Another means of increasing the number of carbohydrate moieties on the antibodies is by chemical or enzymatic coupling of glycosides to the amino acid residues of the antibody. These methods are described in, e.g., WO 87/05330, and Aplin and Wriston (1981) CRC Crit. Rev. Biochem. 22:259-306. Removal of any carbohydrate moieties present on the antibodies can be accomplished chemically or enzymatically as described in the art (Hakimuddin et al. (1987) Arch. Biochem. Biophys. 259:52; Edge et al. (1981) Anal. Biochem. 118:131; and Thotakura et al. (1987) Meth. Enzymol. 138:350). See, e.g., U.S. Pat. No. 5,869,046 for a modification that increases in vivo half-life by providing a salvage receptor binding epitope.

The antibodies can be in the form of full length antibodies, or in the form of fragments of antibodies, e.g., Fab, F(ab')$_2$, Fd, dAb, and scFv fragments. Additional forms include a protein that includes a single variable domain, e.g., a camel or camelized domain. See, e.g., U.S. 2005-0079574 and Davies et al. (1996) Protein Eng. 9(6):531-7.

In one embodiment, the antibody is an antigen-binding fragment of a full length antibody, e.g., a Fab, F(ab')2, Fv or a single chain Fv fragment. Typically, the antibody is a full length antibody. The antibody can be a monoclonal antibody or a mono-specific antibody.

In another embodiment, the antibody can be a human, humanized, CDR-grafted, chimeric, mutated, affinity matured, deimmunized, synthetic or otherwise in vitro-generated antibody, and combinations thereof.

The heavy and light chains of the antibody can be substantially full-length. The protein can include at least one, and preferably two, complete heavy chains, and at least one, and preferably two, complete light chains) or can include an antigen-binding fragment (e.g., a Fab, F(ab')2, Fv or a single chain Fv fragment). In yet other embodiments, the antibody has a heavy chain constant region chosen from, e.g., IgG1, IgG2, IgG3, IgG4, IgM, IgA1, IgA2, IgD, and IgE; particularly, chosen from, e.g., IgG1, IgG2, IgG3, and IgG4, more particularly, IgG1 (e.g., human IgG1). Typically, the heavy chain constant region is human or a modified form of a human constant region. In another embodiment, the antibody has a light chain constant region chosen from, e.g., kappa or lambda, particularly, kappa (e.g., human kappa).

Receptors

Another class of polypeptides that have been shown to be effective as pharmaceutical and/or commercial agents includes receptors. Receptors are typically trans-membrane glycoproteins that function by recognizing an extra-cellular signaling ligand. Receptors typically have a protein kinase domain in addition to the ligand recognizing domain, which initiates a signaling pathway by phosphorylating target intracellular molecules upon binding the ligand, leading to developmental or metabolic changes within the cell. In one embodiment, the receptors of interest are modified so as to remove the transmembrane and/or intracellular domain(s), in place of which there can optionally be attached an Ig-domain. In one embodiment, receptors to be produced in accordance with the present invention are receptor tyrosine kinases (RTKs). The RTK family includes receptors that are crucial for a variety of functions numerous cell types (see, e.g., Yarden and Ullrich, Ann. Rev. Biochem. 57:433-478, 1988; Ullrich and Schlessinger, Cell 61:243-254, 1990, incorporated herein by reference). Non-limiting examples of RTKs include members of the fibroblast growth factor (FGF) receptor family, members of the epidermal growth factor receptor (EGF) family, platelet derived growth factor (PDGF) receptor, tyrosine kinase with immunoglobulin and EGF homology domains-1 (TIE-1) and TIE-2 receptors (Sato et al., Nature 376(6535):70-74 (1995), incorporated herein by reference) and c-Met receptor, some of which have been suggested to promote angiogenesis, directly or indirectly (Mustonen and Alitalo, J. Cell Biol. 129:895-898, 1995). Other non-limiting examples of RTK's include fetal liver kinase 1 (FLK-1) (sometimes referred to as kinase insert domain-containing receptor (KDR) (Terman et al., Oncogene 6:1677-83, 1991) or vascular endothelial cell growth factor receptor 2 (VEGFR-2)), fms-like tyrosine kinase-1 (Flt-1) (DeVries et al. Science 255; 989-991, 1992; Shibuya et al., Oncogene 5:519-524, 1990), sometimes referred to as vascular endothelial cell growth factor receptor 1 (VEGFR-1), neuropilin-1, endoglin, endosialin, and Ax1. Those of ordinary skill in the art will be aware of other receptors that can be expressed in accordance with the present invention.

Growth Factors and Other Signaling Molecules

Another class of polypeptides that have been shown to be effective as pharmaceutical and/or commercial agents includes growth factors and other signaling molecules. Growth factors are typically glycoproteins that are secreted by cells and bind to and activate receptors on other cells, initiating a metabolic or developmental change in the receptor cell.

Non-limiting examples of mammalian growth factors and other signaling molecules include cytokines; epidermal growth factor (EGF); platelet-derived growth factor (PDGF); fibroblast growth factors (FGFs) such as aFGF and bFGF; transforming growth factors (TGFs) such as TGF-alpha and TGF-beta, including TGF-beta 1, TGF-beta 2, TGF-beta 3, TGF-beta 4, or TGF-beta 5; insulin-like growth factor-I and-II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and-gamma; colony stimulating factors (CSFs), e.g., M-CSF, GM-CSF, and G-CSF; interleukins (TLs), e.g., IL-1 to IL-10; tumor necrosis factor (TNF) alpha and beta;

insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin, hemopoietic growth factor; enkephalinase; RANTES (regulated on activation normally T-cell expressed and secreted); human macrophage inflammatory protein (MIP-1-alpha); mullerian-inhibiting substance; relaxin A-chain; relaxin B-chain; prorelaxin; mouse gonadotropin-associated peptide; neurotrophic factors such as bone-derived neurotrophic factor (BDNF), neurotrophin-3, -4, -5, or-6 (NT-3, NT-4, NT-5, or NT-6), or a nerve growth factor such as NGF-beta. One of ordinary skill in the art will be aware of other growth factors or signaling molecules that can be expressed in accordance with the present invention.

G-Protein Coupled Receptors

Another class of polypeptides that have been shown to be effective as pharmaceutical and/or commercial agents includes growth factors and other signaling molecules. G-protein coupled receptors (GPCRs) are proteins that have seven transmembrane domains. Upon binding of a ligand to a GPCR, a signal is transduced within the cell which results in a change in a biological or physiological property of the cell.

GPCRs, along with G-proteins and effectors (intracellular enzymes and channels which are modulated by G-proteins), are the components of a modular signaling system that connects the state of intracellular second messengers to extracellular inputs. These genes and gene-products are potential causative agents of disease.

The GPCR protein superfamily now contains over 250 types of paralogues, receptors that represent variants generated by gene duplications (or other processes), as opposed to orthologues, the same receptor from different species. The superfamily can be broken down into five families: Family I, receptors typified by rhodopsin and the beta2-adrenergic receptor and currently represented by over 200 unique members; Family II, the recently characterized parathyroid hormone/calcitonin/secretin receptor family; Family III, the metabotropic glutamate receptor family in mammals; Family IV, the cAMP receptor family, important in the chemotaxis and development of *D. discoideum*; and Family V, the fungal mating pheromone receptors such as STE2.

Cells

Any eukaryotic cell or cell type susceptible to cell culture can be utilized in accordance with the present invention. For example, plant cells, yeast cells, animal cells, insect cells, avian cells or mammalian cells can be utilized in accordance with the present invention. In one embodiment, the eukaryotic cells are capable of expressing a recombinant protein or are capable of producing a recombinant or reassortant virus.

Non-limiting examples of mammalian cells that can be used in accordance with the present invention include BALB/c mouse myeloma line (NSO/1, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); baby hamster kidney cells (BHK, ATCC CCL 10); Chinese hamster ovary cells ±DHFR (CHO, Urlaub and Chasin, *Proc. Natl. Acad. Sci. USA*, 77:4216 (1980)); mouse sertoli cells (TM4, Mather, *Biol. Reprod.*, 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL5 1); TRI cells (Mather et al., *Annals N.Y. Acad. Sci.*, 383:44-68 (1982)); MRC 5 cells; FS4 cells; and a human hepatoma line (Hep G2). In one embodiment, the present invention is used in the culturing of and expression of polypeptides from CHO cell lines. In a specific embodiment, the CHO cell line is the DG44 CHO cell line. In a specific embodiment, the CHO cell line comprises a vector comprising a polynucleotide encoding a glutamine synthetase polypeptide. In a further specific embodiment, the CHO cell line expresses an exogenous glutamine synthetase gene. (See, e.g., Porter et al., *Biotechnol Prog* 26(5):1446-54 (2010).)

Additionally, any number of commercially and non-commercially available hybridoma cell lines that express polypeptides or proteins can be utilized in accordance with the present invention. One skilled in the art will appreciate that hybridoma cell lines might have different nutrition requirements and/or might require different culture conditions for optimal growth and polypeptide or protein expression, and will be able to modify conditions as needed.

The eukaryotic cells according to the present invention can be selected or engineered to produce high levels of protein or polypeptide, or to produce large quantities of virus. Often, cells are genetically engineered to produce high levels of protein, for example by introduction of a gene encoding the protein or polypeptide of interest and/or by introduction of control elements that regulate expression of the gene (whether endogenous or introduced) encoding the polypeptide of interest.

The eukaryotic cells can also be selected or engineered to survive in culture for extended periods of time. For example, the cells can be genetically engineered to express a polypeptide or polypeptides that confer extended survival on the cells. In one embodiment, the eukaryotic cells comprise a transgene encoding the Bcl-2 polypeptide or a variant thereof. See, e.g., U.S. Pat. No. 7,785,880. In a specific embodiment, the cells comprise a polynucleotide encoding the bcl-xL polypeptide. See, e.g., Chiang G G, Sisk W P. 2005. *Biotechnology and Bioengineering* 91(7):779-792.

The eukaryotic cells can also be selected or engineered to modify its posttranslational modification pathways. In one embodiment, the cells are selected or engineered to modify a protein glycolsylation pathway. In a specific embodiment, the cells are selected or engineered to express an aglycosylated protein, e.g., an aglycosylated recombinant antibody. In another specific embodiment, the cells are selected or engineered to express an afucosylated protein, e.g., an afucosylated recombinant antibody.

The eukaryotic cells can also be selected or engineered to allow culturing in serum free medium.

Media

The cell culture of the present invention is prepared in any medium suitable for the particular cell being cultured. In some embodiments, the medium contains e.g., inorganic salts, carbohydrates (e.g., sugars such as glucose, galactose, maltose or fructose), amino acids, vitamins (e.g., B group vitamins (e.g., B12), vitamin A vitamin E, riboflavin, thiamine and biotin), fatty acids and lipids (e.g., cholesterol and steroids), proteins and peptides (e.g., albumin, transferrin, fibronectin and fetuin), serum (e.g., compositions comprising albumins, growth factors and growth inhibitors, such as, fetal bovine serum, newborn calf serum and horse serum), trace elements (e.g., zinc, copper, selenium and tricarboxylic acid intermediates), hydrolysates (hydrolyzed proteins derived from plant or animal sources), and combinations thereof. Commercially available media such as Ham's F10 (Sigma), Minimal Essential Medium ([MEM], Sigma), RPMI-1640 (Sigma), and Dulbecco's Modified Eagle's Medium ([DMEM], Sigma) are exemplary nutrient solutions. In addition, any of the media described in Ham and Wallace, (1979) *Meth. Enz.*, 58:44; Barnes and Sato, (1980) *Anal. Biochem.*, 102:255; U.S. Pat. Nos. 4,767,704; 4,657,866; 4,927,762; 5,122,469 or 4,560,655; International Publication Nos. WO 90/03430; and WO 87/00195; the disclosures of all of which are incorporated herein by reference, can be used as culture media. Any of these media can be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as gentamycin), trace elements (defined as inorganic compounds usually present at final concentrations in the micromolar range) lipids (such as linoleic or other fatty acids) and their suitable carriers, and glucose or an equivalent energy source. In some embodiments the nutrient media is serum-free media, a protein-free media, or a chemically defined media. Any other necessary supplements can also be included at appropriate concentrations that would be known to those skilled in the art.

In one embodiment, the mammalian host cell is a CHO cell and a suitable medium contains a basal medium component such as a DMEM/HAM F-12 based formulation (for composition of DMEM and HAM F12 media, see culture media formulations in American Type Culture Collection Catalogue of Cell Lines and Hybridomas, Sixth Edition, 1988, pages 346-349) with modified concentrations of some components such as amino acids, salts, sugar, and vitamins, recombinant human insulin, hydrolyzed peptone, such as Primatone HS or Primatone RL (Sheffield, England), or the equivalent; a cell protective agent, such as Pluronic F68 or the equivalent pluronic polyol; gentamycin; and trace elements.

The present invention provides a variety of media formulations that, when used in accordance with other culturing steps described herein, minimize, prevent or reverse decreases in cellular viability in the culture caused by culturing in glutamine-free media.

A media formulation of the present invention that has been shown to have beneficial effects on metabolic balance, cell growth and/or viability or on expression of polypeptide or protein comprises hypoxanthine and thymidine, adenosine, and/or corticosteroids. One of ordinary skill in the art will understand that the media formulations of the present invention encompass both defined and non-defined media.

Cell Culture Processes

Various methods of preparing mammalian cells for production of proteins or polypeptides by batch and fed-batch culture are well known in the art. A nucleic acid sufficient to achieve expression (typically a vector containing the gene encoding the polypeptide or protein of interest and any operably linked genetic control elements) can be introduced into the host cell line by any number of well-known techniques. Typically, cells are screened to determine which of the host cells have actually taken up the vector and express the polypeptide or protein of interest. Traditional methods of detecting a particular polypeptide or protein of interest expressed by mammalian cells include but are not limited to immunohistochemistry, immunoprecipitation, flow cytometry, immunofluorescence microscopy, SDS-PAGE, Western blots, enzyme-linked immunosorbentassay (ELISA), high performance liquid chromatography (HPLC) techniques, biological activity assays and affinity chromatography. One of ordinary skill in the art will be aware of other appropriate techniques for detecting expressed polypeptides or proteins. If multiple host cells express the polypeptide or protein of interest, some or all of the listed techniques can be used to determine which of the cells expresses that polypeptide or protein at the highest levels.

Once a cell that expresses the polypeptide or protein of interest has been identified, the cell is propagated in culture by any of the variety of methods well-known to one of ordinary skill in the art. The cell expressing the polypeptide of interest is typically propagated by growing it at a temperature and in a medium that is conducive to the survival, growth and viability of the cell. The initial culture volume can be of any size, but is often smaller than the culture volume of the production bioreactor used in the final production of the polypeptide or protein of interest, and frequently cells are passaged several times in bioreactors of increasing volume prior to seeding the production bioreactor. The cell culture can be agitated or shaken to increase oxygenation of the medium and dispersion of nutrients to the cells. Alternatively or additionally, special sparging devices that are well known in the art can be used to increase and control oxygenation of the culture. In accordance with the present invention, one of ordinary skill in the art will understand that it can be beneficial to control or regulate certain internal conditions of the bioreactor, including but not limited to pH, temperature, oxygenation, etc.

The cell density useful in the methods of the present invention can be chosen by one of ordinary skill in the art. In accordance with the present invention, the cell density can be as low as a single cell per culture volume. In some embodiments of the present invention, starting cell densities can range from about $2 \times 10^2$ viable cells per mL to about $2 \times 10^3$, $2 \times 10^4$, $2 \times 10^5$, $2 \times 10^6$, $5 \times 10^6$ or $10 \times 10^6$ viable cells per mL and higher.

In accordance with the present invention, a cell culture size can be any volume that is appropriate for production of polypeptides. In one embodiment, the volume of the cell culture is at least 500 liters. In other embodiments, the volume of the production cell culture is 10, 50, 100, 250, 1000, 2000, 2500, 5000, 8000, 10,000, 12,000 liters or more, or any volume in between. For example, a cell culture will be 10 to 5,000 liters, 10 to 10,000 liters, 10 to 15,000 liters, 50 to 5,000 liters, 50 to 10,000 liters, or 50 to 15,000 liters, 100 to 5,000 liters, 100 to 10,000 liters, 100 to 15,000 liters, 500 to 5,000 liters, 500 to 10,000 liters, 500 to 15,000 liters, 1,000 to 5,000 liters, 1,000 to 10,000 liters, or 1,000 to 15,000 liters. Or a cell culture will be between about 500 liters and about 30,000 liters, about 500 liters and about 20,000 liters, about 500 liters and about 10,000 liters, about 500 liters and about 5,000 liters, about 1,000 liters and about 30,000 liters, about 2,000 liters and about 30,000 liters, about 3,000 liters and about 30,000 liters, about 5,000 liters and about 30,000 liters, or about 10,000 liters and about 30,000 liters, or a cell culture will be at least about 500 liters, at least about 1,000 liters, at least about 2,000 liters, at least about 3,000 liters, at least about 5,000 liters, at least about 10,000 liters, at least about 15,000 liters, or at least about 20,000 liters.

One of ordinary skill in the art will be aware of and will be able to choose a suitable culture size for use in practicing the present invention. The production bioreactor for the culture can be constructed of any material that is conducive to cell growth and viability that does not interfere with expression or stability of the produced polypeptide or protein.

The temperature of the cell culture will be selected based primarily on the range of temperatures at which the cell culture remains viable. For example, during the initial growth phase, CHO cells grow well at 37° C. In general, most mammalian cells grow well within a range of about 25° C. to 42° C.

In one embodiment of the present invention, the temperature of the initial growth phase is maintained at a single, constant temperature. In another embodiment, the temperature of the initial growth phase is maintained within a range of temperatures. For example, the temperature can be steadily increased or decreased during the initial growth phase. Alternatively, the temperature can be increased or decreased by discrete amounts at various times during the initial growth phase. One of ordinary skill in the art will be able to determine whether a single or multiple temperatures should be used, and whether the temperature should be adjusted steadily or by discrete amounts.

The cells can be grown during the initial growth phase for a greater or lesser amount of time, depending on the needs of the practitioner and the requirement of the cells themselves. In one embodiment, the cells are grown for a period of time sufficient to achieve a viable cell density that is a given percentage of the maximal viable cell density that the cells would eventually reach if allowed to grow undisturbed. For example, the cells can be grown for a period of time sufficient to achieve a desired viable cell density of 1, 5, 10, 15, 20, 25, 30, 35, 40, 45, 50, 55, 60, 65, 70, 75, 80, 85, 90, 95 or 99 percent of maximal viable cell density.

In another embodiment the cells are allowed to grow for a defined period of time. For example, depending on the starting concentration of the cell culture, the temperature at which the cells are grown, and the intrinsic growth rate of the cells, the cells can be grown for 0, 1, 2, 3, 4, 5, 6, 7, 8, 9, 10, 11, 12, 13, 14, 15, 16, 17, 18, 19, 20 or more days. In some cases, the cells can be allowed to grow for a month or more. In one embodiment, the growth phase is between about 1 day and about 20 days, about 1 day and about 15 days, about 1 day and about 14 days, about 1 day and about 13 days, about 1 day and about 12 days, about 1 day and about 11 days, about 1 day and about 10 days, about 1 day and about 9 days, about 1 day and about 8 days, about 1 day and about 7 days, about 1 day and about 6 days, about 1 day and about 5 days, about 1 day and about 4 days, about 1 day and about 3 days, about 2 days and about 15 days, about 3 days and about 15 days, about 4 days and about 15 days, about 5 days and about 15 days, about 6 days and about 15 days, about 7 days and about 15 days, about 8 days and about 15 days, about 9 days and about 15 days, about 10 days and about 15 days, about 2 days and about 20 days, about 3 days and about 20 days, about 4 days and about 20 days, about 5 days and about 20 days, about 6 days and about 20 days, about 7 days and about 20 days, about 8 days and about 20 days, about 9 days and about 20 days, about 10 days and about 20 days, or about 10 days and about 20 days. In another embodiment, the growth phase is at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 15 days, or at least about 20 days. In a further embodiment, the growth phase is about 1 day, about 2 days, about 3 days, about 4 days, about 5 days, about 6 days, about 7 days, about 8 days, about 9 days, about 10 days, about 11 days, about 12 days, about 15 days, or about 20 days.

The cells would be grown for 0 days in the production bioreactor if their growth in a seed bioreactor, at the initial growth phase temperature, was sufficient that the viable cell density in the production bioreactor at the time of its inoculation is already at the desired percentage of the maximal viable cell density. The practitioner of the present invention will be able to choose the duration of the initial growth phase depending on polypeptide or protein production requirements and the needs of the cells themselves.

The cell culture can be agitated or shaken during the initial culture phase in order to increase oxygenation and dispersion of nutrients to the cells. In accordance with the present invention, one of ordinary skill in the art will understand that it can be beneficial to control or regulate certain internal conditions of the bioreactor during the initial growth phase, including but not limited to pH, temperature, oxygenation, etc. For example, pH can be controlled by supplying an appropriate amount of acid or base and oxygenation can be controlled with sparging devices that are well known in the art.

In one embodiment, at the end of the initial growth phase, at least one of the culture conditions is shifted so that a second set of culture conditions is applied. The shift in culture conditions can be accomplished by a change in the temperature, pH, osmolality or chemical inductant level of the cell culture. In one embodiment, the culture conditions are shifted by shifting the temperature of the culture.

When shifting the temperature of the culture, the temperature shift can be relatively gradual. For example, it can take several hours or days to complete the temperature change. Alternatively, the temperature shift can be relatively abrupt. For example, the temperature change can be complete in less than several hours. Given the appropriate production and control equipment, such as is standard in the commercial large-scale production of polypeptides or proteins, the temperature change can even be complete within less than an hour.

The temperature of the cell culture in the subsequent growth phase will be selected based primarily on the range of temperatures at which the cell culture remains viable and expresses recombinant polypeptides or proteins at commercially adequate levels. In general, most mammalian cells remain viable and express recombinant polypeptides or proteins at commercially adequate levels within a range of about 25° C. to 42° C. In one embodiment, mammalian cells remain viable and express recombinant polypeptides or proteins at commercially adequate levels within a range of about 25° C. to 35° C. Those of ordinary skill in the art will be able to select appropriate temperature or temperatures in which to grow cells, depending on the needs of the cells and the production requirements of the practitioner.

In accordance with the present invention, once the conditions of the cell culture have been shifted as discussed above, the cell culture is maintained for a subsequent production phase under a second set of culture conditions conducive to the survival and viability of the cell culture and appropriate for expression of the desired polypeptide or protein at commercially adequate levels.

As discussed above, the culture can be shifted by shifting one or more of a number of culture conditions including, but not limited to, temperature, pH, osmolality, and sodium butyrate levels. In one embodiment, the temperature of the culture is shifted. According to this embodiment, during the subsequent production phase, the culture is maintained at a temperature or temperature range that is lower than the temperature or temperature range of the initial growth phase. For example, during the subsequent production phase, CHO cells express recombinant polypeptides and proteins well within a range of 25° C. to 35° C.

In accordance with the present invention, the cells can be maintained in the subsequent production phase until a desired cell density or production titer is reached. In one embodiment, the cells are maintained in the subsequent production phase until the titer to the recombinant polypeptide or protein reaches a maximum. In other embodiments, the culture can be harvested prior to this point, depending on the production requirement of the practitioner or the needs of the cells themselves. For example, the cells can be maintained for a period of time sufficient to achieve a viable cell density of 1, 5, 10, 15, 20, 25, 30, 35, 40, 45, 50, 55, 60, 65, 70, 75, 80, 85, 90, 95 or 99 percent of maximal viable cell density. In some cases, it is desirable to allow the viable cell density to reach a maximum, and then allow the viable cell density to decline to some level before harvesting the culture. In an extreme example, it can be desirable to allow the viable cell density to approach or reach zero before harvesting the culture.

In another embodiment of the present invention, the cells are allowed to grow for a defined period of time during the subsequent production phase. For example, depending on the concentration of the cell culture at the start of the subsequent growth phase, the temperature at which the cells are grown, and the intrinsic growth rate of the cells, the cells can be grown for 1, 2, 3, 4, 5, 6, 7, 8, 9, 10, 11, 12, 13, 14, 15, 16, 17, 18, 19, 20 or more days. In some cases, the cells can be allowed to grow for a month or more. The practitioner of the present invention will be able to choose the duration of the subsequent production phase depending on polypeptide or protein production requirements and the needs of the cells themselves.

In certain cases, it can be beneficial or necessary to supplement the cell culture during the growth and/or subsequent production phase with nutrients or other medium components that have been depleted or metabolized by the cells. For example, it might be advantageous to supplement the cell culture with nutrients or other medium components observed to have been depleted. Alternatively or additionally, it can be beneficial or necessary to supplement the cell culture prior to the subsequent production phase. As non-limiting examples, it can be beneficial or necessary to supplement the cell culture with hormones and/or other growth factors, particular ions (such as sodium, chloride, calcium, magnesium, and phosphate), buffers, vitamins, nucleosides or nucleotides, trace elements (inorganic compounds usually present at very low final concentrations), amino acids, lipids, or glucose or other energy source.

These supplementary components, including the amino acids, can all be added to the cell culture at one time, or they can be provided to the cell culture in a series of additions. In one embodiment of the present invention, the supplementary components are provided to the cell culture at multiple times in proportional amounts. In another embodiment, it can be desirable to provide only certain of the supplementary components initially, and provide the remaining components at a later time. In yet another embodiment of the present invention, the cell culture is fed continually with these supplementary components.

In accordance with the present invention, the total volume added to the cell culture should optimally be kept to a minimal amount. For example, the total volume of the medium or solution containing the supplementary components added to the cell culture can be 1, 2, 3, 4, 5, 6, 7, 8, 9, 10, 15, 20, 25, 30, 35, 40, 45 or 50% of the volume of the cell culture prior to providing the supplementary components.

The cell culture can be agitated or shaken during the subsequent production phase in order to increase oxygenation and dispersion of nutrients to the cells. In accordance with the present invention, one of ordinary skill in the art will understand that it can be beneficial to control or regulate certain internal conditions of the bioreactor during the subsequent growth phase, including but not limited to pH, temperature, oxygenation, etc. For example, pH can be controlled by supplying an appropriate amount of acid or base and oxygenation can be controlled with sparging devices that are well known in the art.

In certain embodiments of the present invention, the practitioner can find it beneficial or necessary to periodically monitor particular conditions of the growing cell culture. Monitoring cell culture conditions allows the practitioner to determine whether the cell culture is producing recombinant polypeptide or protein at suboptimal levels or whether the culture is about to enter into a suboptimal production phase.

In order to monitor certain cell culture conditions, it will be necessary to remove small aliquots of the culture for analysis. One of ordinary skill in the art will understand that such removal can potentially introduce contamination into the cell culture, and will take appropriate care to minimize the risk of such contamination.

As non-limiting example, it can be beneficial or necessary to monitor temperature, pH, cell density, cell viability, integrated viable cell density, lactate levels, ammonium levels, osmolarity, or titer of the expressed polypeptide or protein. Numerous techniques are well known in the art that will allow one of ordinary skill in the art to measure these conditions. For example, cell density can be measured using a hemacytometer, a Coulter counter, or Cell density examination (CEDEX). Viable cell density can be determined by staining a culture sample with Trypan blue. Since only dead cells take up the Trypan blue, viable cell density can be determined by counting the total number of cells, dividing the number of cells that take up the dye by the total number of cells, and taking the reciprocal. HPLC can be used to determine the levels of lactate, ammonium or the expressed polypeptide or protein. Alternatively, the level of the expressed polypeptide or protein can be determined by standard molecular biology techniques such as coomassie staining of SDS-PAGE gels, Western blotting, Bradford assays, Lowry assays, Biuret assays, and UV absorbance. It can also be beneficial or necessary to monitor the posttranslational modifications of the expressed polypeptide or protein, including phosphorylation and glycosylation.

The practitioner can also monitor the metabolic status of the cell culture, for example, by monitoring the glucose, lactate, ammonium, and amino acid concentrations in the cell culture, as well as by monitoring the oxygen production or carbon dioxide production of the cell culture. For example, cell culture conditions can be analyzed by using NOVA Bioprofile 100 or 400 (NOVA Biomedical, WA). Additionally, the practitioner can monitor the metabolic state of the cell culture by monitoring the activity of mitochondria. In embodiment, mitochondrial activity can be monitored by monitoring the mitochondrial membrane potential using Rhodamine 123. Johnson L V, Walsh M L, Chen L B. 1980. *Proceedings of the National Academy of Sciences* 77(2):990-994.

Isolation of Expressed Polypeptide

In general, it will typically be desirable to isolate and/or purify proteins or polypeptides expressed according to the present invention. In one embodiment, the expressed polypeptide or protein is secreted into the medium and thus cells and other solids can be removed, as by centrifugation or filtering for example, as a first step in the purification process.

Alternatively, the expressed polypeptide can be bound to the surface of the host cell. In this embodiment, the media is removed and the host cells expressing the polypeptide or protein are lysed as a first step in the purification process. Lysis of mammalian host cells can be achieved by any number of means well known to those of ordinary skill in the art, including physical disruption by glass beads and exposure to high pH conditions.

The polypeptide can be isolated and purified by standard methods including, but not limited to, chromatography (e.g., ion exchange, affinity, size exclusion, and hydroxyapatite chromatography), gel filtration, centrifugation, or differential solubility, ethanol precipitation or by any other available technique for the purification of proteins (See, e.g., Scopes, Protein Purification Principles and Practice 2nd Edition, Springer-Verlag, New York, 1987; Higgins, S. J. and Hames, B. D. (eds.), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol 182), Academic Press, 1997, all incorporated herein by reference). For immunoaffinity chromatography in particular, the protein can be isolated by binding it to an affinity column comprising antibodies that were raised against that protein and were affixed to a stationary support. Alternatively, affinity tags such as an influenza coat sequence, poly-histidine, or glutathione-S-transferase can be attached to the protein by standard recombinant techniques to allow for easy purification by passage over the appropriate affinity column. Protease inhibitors such as phenyl methyl sulfonyl fluoride (PMSF), leupeptin, pepstatin or aprotinin can be added at any or all stages in order to reduce or eliminate degradation of the polypeptide or protein during the purification process. Protease inhibitors are particularly desired when cells must be lysed in order to isolate and purify the expressed polypeptide or protein. One of ordinary skill in the art will appreciate that the exact purification technique will vary depending on the character of the polypeptide or protein to be purified, the character of the cells from which the polypeptide or protein is expressed, and the composition of the medium in which the cells were grown.

Pharmaceutical Compositions

A polypeptide can be formulated as a pharmaceutical composition for administration to a subject, e.g., to treat or prevent a disorder or disease. Typically, a pharmaceutical composition includes a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. The composition can include a pharmaceutically acceptable salt, e.g., an acid addition salt or a base addition salt (See e.g., Berge, S. M., et al. (1977) J. Pharm. Sci. 66:1-19). In one embodiment, a pharmaceutical composition is an immunogenic composition comprising a virus produced in accordance with methods described herein.

Pharmaceutical formulation is a well-established art, and is further described, e.g., in Gennaro (ed.), Remington. The Science and Practice of Pharmacy, 20$^{th}$ ed., Lippincott, Williams & Wilkins (2000) (ISBN: 0683306472); Ansel et al., Pharmaceutical Dosage Forms and Drug Delivery Systems, 7$^{th}$ Ed., Lippincott Williams & Wilkins Publishers (1999) (ISBN: 0683305727); and Kibbe (ed.), Handbook of Pharmaceutical Excipients American Pharmaceutical Association, 3$^{rd}$ ed. (2000) (ISBN: 091733096X).

The pharmaceutical compositions can be in a variety of forms. These include, for example, liquid, semi-solid and solid dosage forms, such as liquid solutions (e.g., injectable and infusible solutions), dispersions or suspensions, tablets, pills, powders, liposomes and suppositories. The form can depend on the intended mode of administration and therapeutic application. Typically compositions for the agents described herein are in the form of injectable or infusible solutions.

In one embodiment, the antibody is formulated with excipient materials, such as sodium chloride, sodium dibasic phosphate heptahydrate, sodium monobasic phosphate, and a stabilizer. It can be provided, for example, in a buffered solution at a suitable concentration and can be stored at 2-8° C.

Such compositions can be administered by a parenteral mode (e.g., intravenous, subcutaneous, intraperitoneal, or intramuscular injection). The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The composition can be formulated as a solution, microemulsion, dispersion, liposome, or other ordered structure suitable for stable storage at high concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. In the case of sterile powders for the preparation of sterile injectable solutions, the methods of preparation are vacuum drying and freeze drying that yield a powder of an agent described herein plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In certain embodiments, the polypeptide can be prepared with a carrier that will protect the compound against rapid release, such as a controlled release formulation, including implants, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known. See, e.g., Sustained and Controlled Release Drug Delivery Systems, J. R. Robinson, ed., Marcel Dekker, Inc., New York (1978).

The foregoing description is to be understood as being representative only and is not intended to be limiting.

Alternative methods and materials for implementing the invention and also additional applications will be apparent to one of skill in the art, and are intended to be included within the accompanying claims.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, 2nd Ed., Sambrook et al., ed., Cold Spring Harbor Laboratory Press: (1989); *Molecular Cloning: A Laboratory Manual*, Sambrook et al., ed., Cold Springs Harbor Laboratory, New York (1992), DNA Cloning, D. N. Glover ed., Volumes I and II (1985); *Oligonucleotide Synthesis*, M. J. Gait ed., (1984); Mullis et al. U.S. Pat. No. 4,683,195; *Nucleic Acid Hybridization*, B. D. Hames & S. J. Higgins eds. (1984); *Transcription And Translation*, B. D. Hames & S. J. Higgins eds. (1984); *Culture Of Animal Cells*, R. I. Freshney, Alan R. Liss, Inc., (1987); *Immobilized Cells And Enzymes*, IRL Press, (1986); B. Perbal, *A Practical Guide To Molecular Cloning* (1984); the treatise, *Methods In Enzymology*, Academic Press, Inc., N.Y.; *Gene Transfer Vectors For Mammalian Cells*, J. H. Miller and M. P. Calos eds., Cold Spring Harbor Laboratory (1987); *Methods In Enzymology*, Vols. 154 and 155 (Wu et al. eds.); *Immunochemical Methods In Cell And Molecular Biology*, Mayer and Walker, eds., Academic Press, London (1987); *Handbook Of Experimental Immunology*, Volumes I-IV, D. M. Weir and C. C. Blackwell, eds., (1986); *Manipulating the Mouse Embryo*, Cold Spring Harbor Laboratory Press, Cold Spring Harbor, N.Y., (1986); and in Ausubel et al., *Current Protocols in Molecular Biology*, John Wiley and Sons, Baltimore, Md. (1989).

General principles of antibody engineering are set forth in *Antibody Engineering*, 2nd edition, C. A. K. Borrebaeck, Ed., Oxford Univ. Press (1995). General principles of protein engineering are set forth in *Protein Engineering, A Practical Approach*, Rickwood, D., et al., Eds., IRL Press at Oxford Univ. Press, Oxford, Eng. (1995). General principles of antibodies and antibody-hapten binding are set forth in: Nisonoff, A., *Molecular Immunology*, 2nd ed., Sinauer Associates, Sunderland, Mass. (1984); and Steward, M. W., *Antibodies, Their Structure and Function*, Chapman and Hall, New York, N.Y. (1984). Additionally, standard methods in immunology known in the art and not specifically described are generally followed as in *Current Protocols in Immunology*, John Wiley & Sons, New York; Stites et al. (eds), *Basic and Clinical-Immunology* (8th ed.), Appleton & Lange, Norwalk, Conn. (1994) and Mishell and Shiigi (eds), *Selected Methods in Cellular Immunology*, W.H. Freeman and Co., New York (1980).

Standard reference works setting forth general principles of immunology include *Current Protocols in Immunology*, John Wiley & Sons, New York; Klein, J., Immunology: *The Science of Self-Nonself Discrimination*, John Wiley & Sons, New York (1982); Kennett, R., et al., eds., *Monoclonal Antibodies, Hybridoma: A New Dimension in Biological Analyses*, Plenum Press, New York (1980); Campbell, A., "Monoclonal Antibody Technology" in Burden, R., et al., eds., *Laboratory Techniques in Biochemistry and Molecular Biology*, Vol. 13, Elsevere, Amsterdam (1984), *Kuby Immunology* $4^{th}$ ed. Ed. Richard A. Goldsby, Thomas J. Kindt and Barbara A. Osborne, H. Freemand & Co. (2000); Roitt, I., Brostoff, J. and Male D., Immunology 6th ed. London: Mosby (2001); Abbas A., Abul, A. and Lichtman, A., *Cellular and Molecular Immunology Ed.* 5, Elsevier Health Sciences Division (2005); Kontermann and Dubel, *Antibody Engineering*, Springer Verlan (2001); Sambrook and Russell, *Molecular Cloning: A Laboratory Manual*. Cold Spring Harbor Press (2001); Lewin, Genes VIII, Prentice Hall (2003); Harlow and Lane, *Antibodies: A Laboratory Manual*, Cold Spring Harbor Press (1988); Dieffenbach and Dveksler, *PCR Primer* Cold Spring Harbor Press (2003).

All of the references cited above, as well as all references cited herein, are incorporated herein by reference in their entireties.

EXAMPLES

Example 1-Addition of Hypoxanthine and Thymidine (HT) to Glutamine-Free Media Maintains Cell Viability Cell line: The cell line used in this study produced a growth factor receptor immunoadhesin polypeptide. The cell line was constructed using DG44 adapted to grow in serum-free medium (Prentice, 2007).

Culture medium: Basal and feed medium used for this experiment are both proprietary in-house media that were previously described in Huang, 2010 and Kshirsagar, 2012. Both media are chemically defined. Briefly the basal medium CM3 was used for all maintenance stages. A modified version of CM3v2, with additional hypoxanthine and thymidine, and optionally corticosteroids, or with additional adenosine, was used for the production stage. This medium contains glucose, amino acids, vitamins, minerals, and trace elements necessary for the robust cultivation of mammalian cells. Feed medium is a more concentrated version of the basal medium with the nutritional content optimized to maximize growth and productivity. No lactate is present in the feed medium.

Cell culture methods: Cells were thawed and maintained as in a previous report (Kshirsagar, et al. 2012 Biotechnol Bioeng, Huang, et al. *Biotechnology Progress* 26(5):1400-1410 (2010)). Basal medium for thaw and passing was the same as in previous reports (Kshirsagar/Huang). Briefly, cells were thawed and maintained in 3 L shake flasks (Corning Life Sciences, Corning, N.Y.) with 1 L working volumes and were passaged every 2-3 days. For maintenance cultures the incubator was controlled at 36° C. and 5% $CO_2$.

Bioreactor culture conditions: Fed batch cultures were performed in 5 L glass Applikon vessels using Finesse TruBio DV controllers (Finesse Solutions, San Jose, Calif.) with an initial working volume between 2-2.5 L. Bioreactors were seeded at constant seed density of $4 \times 10^5$ cells/ml. Concentrated feed medium was delivered on days 3, 5, and every day following through harvest. Temperature was maintained at 36° C. and pH was controlled at 7.1+/−0.2 by the addition of either 1 M sodium carbonate or carbon dioxide. Dissolved oxygen was maintained at 30% by air and oxygen sparge using a drilled hole sparger. Agitation was maintained between 200-400 RPM throughout the culture to limit total gas flow, while an overlay was maintained between 0.005 and 0.04 vvm.

Offline analysis: Samples were taken on most days and analyzed with a variety of equipment. Cell density and viability were measured using the standard technique of trypan blue exclusion using a Cedex (Roche Innovatis AG, Germany). Cell viability and growth rate of the various cultures were measured during the culture time course at specific days post-inoculation.

In order to investigate the effect of hypoxanthine and thymidine, optionally in the presence of corticosteroids, 100 μM hypoxanthine and 16 μM thymidine were added to the production medium on day 0. In some cases, 2.5 μM corticosteroid was also provided.

The viability of cells expressing the immunoadhesin in glutamine-containing media is typically greater than 95%. However, when transitioned from glutamine-containing to glutamine-free media in several passages using fixed 1:5 volume split ratios, viability dropped sharply to <90% and very slowly recovered (FIG. 1). The addition of 100 μM hypoxanthine and 16 μM thymidine prevented the viability drop.

The growth rate of immunoadhesin-expressing cells in glutamine-containing media is approximately 0.65/day. However, when transitioned from glutamine-containing to glutamine-free media, cellular growth rates dropped sharply to approximately 0.30/day and very slowly increased with further passaging/adaptation (FIG. 2).

Example 2-Addition of Corticosteroids to Glutamine-Free Media Hastens Recovery of Cell Viability Corticosteroids have been shown to increase the expression of glutamine synthetase. Dexamethasone, hydrocortisone, and prednisolone were added to cells cultured in glutamine-free media at a concentration of 2.5 μM. All corticosteroids prevented the sharp viability drop seen in the control condition and shortened the viability recovery period (FIG. 3). Supplementation of 2 mM glutamate and ammonia ($NH_4Glu$), the substrates for glutamine synthetase, in addition to the corticosteroids resulted in slightly improved growth rates as well as higher viability (FIGS. 4 and 5).

Example 3-Addition of Hypoxanthine, Thymidine, and Corticosteroids Maintains Cell Growth and Viability During Transition to Glutamine-Free Media Mammalian cells expressing an immunoadhesin were transferred from glutamine-containing media to glutamine-free media using a 1:5 split ratio on Day 0. 100 μM hypoxanthine, 16 μM thymidine, and corticosteroids (25 μM dexamethasone, 25 μM prednisolone) were supplemented in combination for cell transition from glutamine-containing media to glutamine-free media (FIG. 6). The results show that the benefits derived from hypoxanthine and thymidine (HT) and corticosteroid supplementation were additive, with much of the benefit derived from the HT supplementation.

Example 4-Addition of Hypoxanthine and Thymidine (HT) or Adenosine, Maintains the Growth and the Viability of Anti Alpha-Synuclein CHO Cells During Transition to Glutamine-Free Media Anti alpha-synuclein CHO cells were transferred from glutamine-containing media to glutamine-free media using a 1:5 split ratio on Day 0. Addition of HT or adenosine to anti alpha-synuclein CHO cells aided in the transition from glutamine-containing media to glutamine-free media (FIG. 7). Although the anti alpha-synuclein cells did not exhibit the viability decline observed in the immunoadhesin-expressing mammalian cells used in Examples 1-3, the growth rate declined. Addition of HT or adenosine boosted the transitional growth rate. There was a concentration-dependent response, as 500 μM supplementation appeared to be slightly toxic compared to the 100 μM supplementation. The anti alpha-synuclein cells showed faster recovery compared to the immunoadhesin-expressing mammalian cells with the unassisted 0 mM glutamine growth rate recovering after three passages. HT aided in recovery, but the effect was not as dramatic as that observed in the immunoadhesin-expressing mammalian cells.

The present invention is not to be limited in scope by the specific embodiments described which are intended as single illustrations of individual aspects of the invention, and any compositions or methods which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

All documents, articles, publications, patents, and patent applications mentioned in this specification are herein incorporated by reference to the same extent as if each individual publication or patent application was specifically and individually indicated to be incorporated by reference.

What is claimed is:

1. A method of producing a polypeptide of interest in a glutamine-free cell culture medium, the method comprising culturing mammalian cells expressing the polypeptide of interest in the glutamine-free cell culture medium under conditions that support expression of the polypeptide of interest, wherein said glutamine-free cell culture medium comprises between about 20 μM and about 1000 μM hypoxanthine and between about 2 μM and about 1000 μM thymidine.

2. The method of claim 1, further comprising supplementing the glutamine-free cell culture medium with between about 10 μM and about 1000 μM adenosine.

3. The method of claim 1, wherein the mammalian cells are initially maintained in a culture medium containing glutamine, and are transitioned to the glutamine-free cell culture medium for production phase.

4. The method of claim 1, wherein the glutamine-free cell culture medium further comprises at least one corticosteroid.

5. The method of claim 4, wherein the at least one corticosteroid is present at a concentration of between about 0.5 μM and about 500 μM.

6. The method of claim 4, further comprising supplementing the glutamine-free cell culture medium with a feed medium comprising a sufficient amount of at least one corticosteroid to increase the corticosteroid concentration in the glutamine-free cell culture medium to between about 0.5 μM and about 500 μM.

7. The method of claim 1, wherein the glutamine-free cell culture medium comprises about 100 μM hypoxanthine and about 16 μM thymidine.

8. The method of claim 7, wherein the glutamine-free cell culture medium further comprises adenosine.

9. The method of claim 1, wherein the mammalian cells are maintained for between about 1 day and about 120 days.

10. The method of claim 1, wherein the glutamine-free cell culture medium is supplemented with the feed medium between about 1 and about 25 times.

11. The method of claim 1, wherein the mammalian cells have been genetically modified to alter their innate glycosylation pathways or to increase their life-span in culture.

12. The method of claim 1, wherein the polypeptide of interest is selected from the group consisting of: an antibody, an immunoadhesin, a Transforming Growth Factor (TGF)

beta superfamily signaling molecule, and a blood clotting factor, optionally wherein the immunoadhesin comprises tumor necrosis factor receptor.

13. The method of claim 1, wherein the total amount of polypeptide of interest produced by the mammalian cells is higher than the total amount of polypeptide of interest produced by the mammalian cells maintained in a glutamine-free culture medium that is substantially free from hypoxanthine or thymidine, and wherein the total amount of polypeptide of interest produced by the mammalian cells is between about 5% and about 500% higher than the total amount of polypeptide of interest produced by the mammalian cells maintained in a glutamine-free cell culture medium that is substantially free from hypoxanthine or thymidine.

14. The method of claim 1, wherein the specific productivity of the mammalian cells is higher than the specific productivity of mammalian cells maintained in a glutamine-free cell culture medium that is substantially free from hypoxanthine or thymidine.

15. The method of claim 8, wherein the glutamine-free cell culture medium comprises about 100 µM adenosine.

16. The method of claim 1, wherein the glutamine-free cell culture medium further comprises at least one corticosteroid and adenosine.

17. The method of claim 16, wherein the total amount of polypeptide of interest produced by the mammalian cells is higher than the total amount of polypeptide of interest produced by the mammalian cells maintained in a glutamine-free culture medium that is substantially free from hypoxanthine, thymidine, adenosine, or corticosteroids, and wherein the total amount of polypeptide of interest produced by the mammalian cells is between about 5% and about 500% higher than the total amount of polypeptide of interest produced by the mammalian cells maintained in a glutamine-free cell culture medium that is substantially free from hypoxanthine, thymidine, adenosine, or corticosteroids.

18. The method of claim 16, wherein the specific productivity of the mammalian cells is higher than the specific productivity of mammalian cells maintained in a glutamine-free cell culture medium that is substantially free from hypoxanthine, thymidine, adenosine, or corticosteroids.

* * * * *